(12) United States Patent
Eliyahu et al.

(10) Patent No.: US 11,618,893 B2
(45) Date of Patent: Apr. 4, 2023

(54) ANC80 ENCODING SPHINGOLIPID-METABOLIZING PROTEINS FOR MITIGATING DISEASE-INDUCED TISSUE DAMAGE

(71) Applicant: Icahn School of Medicine at Mount Sinai, New York, NY (US)

(72) Inventors: Efrat Eliyahu, New York, NY (US); Adam Vincek, New York, NY (US); Anthony Fargnoli, New York, NY (US); Michael Katz, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 154 days.

(21) Appl. No.: 16/567,771

(22) Filed: Sep. 11, 2019

(65) Prior Publication Data
US 2020/0002696 A1    Jan. 2, 2020

Related U.S. Application Data

(63) Continuation-in-part of application No. PCT/US2019/021201, filed on Mar. 7, 2019.

(60) Provisional application No. 62/692,185, filed on Jun. 29, 2018.

(51) Int. Cl.
| | |
|---|---|
| *C12N 9/80* | (2006.01) |
| *C12N 15/86* | (2006.01) |
| *C12N 15/52* | (2006.01) |
| *A61K 48/00* | (2006.01) |

(52) U.S. Cl.
CPC ............ *C12N 9/80* (2013.01); *A61K 48/005* (2013.01); *C12N 15/52* (2013.01); *C12N 15/86* (2013.01); *C12N 2750/14143* (2013.01); *C12Y 305/01023* (2013.01)

(58) Field of Classification Search
CPC .......... C12N 9/80; C12N 15/86; C12N 15/52; C12N 2750/14143; A61K 48/005; A61K 48/0075; C12Y 305/01023; C12Y 207/01091; A01K 2227/105; A01K 2227/103; A01K 2267/0375; A01K 2207/30
See application file for complete search history.

(56) References Cited

U.S. PATENT DOCUMENTS

| | | | |
|---|---|---|---|
| 8,697,359 | B1 | 4/2014 | Zhang |
| 8,961,962 | B2 | 2/2015 | Schuchman et al. |
| 9,695,220 | B2 | 7/2017 | Vandenberghe et al. |
| 2002/0099029 | A1 | 7/2002 | Liau et al. |
| 2008/0199450 | A1 | 8/2008 | Schuchman et al. |
| 2012/0039812 | A1 | 2/2012 | Holsboer et al. |
| 2013/0259924 | A1 | 10/2013 | Bancel et al. |
| 2014/0287015 | A1 | 9/2014 | Schuchman et al. |
| 2016/0038574 | A1* | 2/2016 | Schuchman ............ A61P 43/00 424/450 |
| 2017/0044516 | A1 | 2/2017 | Tsai et al. |
| 2017/0332610 | A1 | 11/2017 | Voronina et al. |
| 2017/0356060 | A1 | 12/2017 | Murillo Sauca et al. |
| 2018/0008679 | A1 | 1/2018 | Niklason et al. |
| 2018/0066252 | A1 | 3/2018 | Patel et al. |
| 2019/0117733 | A1 | 4/2019 | Chien et al. |
| 2019/0216730 | A1 | 7/2019 | Heartlein et al. |

FOREIGN PATENT DOCUMENTS

| | | |
|---|---|---|
| WO | 2008086296 A2 | 7/2008 |
| WO | 2013151663 A1 | 10/2013 |
| WO | 2013185069 A1 | 12/2013 |
| WO | 2014140051 A1 | 9/2014 |
| WO | 2017153936 A1 | 9/2017 |
| WO | 2019009979 A1 | 1/2019 |
| WO | 2019173615 A1 | 9/2019 |
| WO | 2019173632 A1 | 9/2019 |
| WO | 2021050064 A1 | 3/2021 |
| WO | 2021050877 A1 | 3/2021 |

OTHER PUBLICATIONS

D'Alto M et al. Pulmonary arterial hypertension associated with congenital heart disease. 2012. European Respiratory Review. vol. 21, No. 26. p. 328-337 (Year: 2012).*
Petrache I et al. Ceramide upregulation causes pulmonary cell apoptosis and emphysema-like disease in mice. 2005. Nature Medicine. vol. 11, No. 5. p. 491-498. (Year: 2005).*
Talati M et al. Fatty acid metabolism in pulmonary arterial hypertension: role in right ventricular dysfunction and hypertrophy. 2015. Pulmonary Circulation. vol. 5, No. 2. p. 269-278. (Year: 2015).*
International Search Report and Written Opinion of the International Searching Authority for International Application No. PCT/US2019/021218 dated Jul. 5, 2019.
International Search Report and Written Opinion of the International Searching Authority for International Application No. PCT/US2019/021189 dated Jun. 14, 2019.
International Search Report and Written Opinion of the International Searching Authority for International Application No. PCT/US2019/021201 dated Aug. 5, 2019.
Blaho, V.A., et al., "An update on the biology of sphingosine 1-phosphate receptors", Journal of Lipid Research, vol. 55, pp. 1596-1608 (2014).
Cannavo, A., et al., "Sphingosine Kinases and Sphingosine 1-Phosphate Receptors: Signaling and Actions in the Cardiovascular System", vol. 8, Article 556, pp. 1-12 (2017).
Eliyahu, E., et al., "Acid ceramidase improves the quality of oocytes and embryos and the outcome of in vitro fertilization", the FASEB Journal, vol. 24, pp. 1229-1238 (2010).

(Continued)

*Primary Examiner* — Paul J Holland
(74) *Attorney, Agent, or Firm* — Heslin Rothenberg Farley & Mesiti P.C.

(57) ABSTRACT

The present disclosure relates generally to the use of sphingolipid-metabolizing proteins to mitigate or minimize tissue damage resulting from injury or from disease, for example, pulmonary arterial hypertension (PAH) when the sphingolipid-metabolizing protein is delivered via expression from an Anc80 vector.

10 Claims, 8 Drawing Sheets

Specification includes a Sequence Listing.

(56) References Cited

OTHER PUBLICATIONS

Ferizi, M., et al., "Human cellular CYBA UTR sequences increase mRNA translation without affecting the half-life of recombinant RNA transcripts", Scientific Reports, 6:39149, pp. 1-13 (2016).
Landegger, L.D., et al., "A synthetic AAV vector enables safe and efficient gene transfer to the mammalian inner ear", Nat Biotechnol., vol. 35, No. 3, pp. 280-284 (2017).
Maceyka, M., et al., "Sphigosine-1-Phosplate Singaling and Its Role in Disease", Trends Cell Biol., vol. 22, No. 1, pp. 50-60 (2012).
Pan, B., et al., "Gene Therapy Restores Auditory and Vestibular Function in a Mouse Model of Usher Syndrome Type 1c", Nat Biotechnol., vol. 35, No. 3, pp. 264-272 (2017).
Ramsubir, S., "Retrovirus-Mediated Gene Therapy for Farber Disease", URL: https://tspace.library.utoronto.ca/bitstream/1807/11249/1/Ramsubir_Shobha_200806_PhD_thesis, pp. 1-149 (2008).
Sugano, E., et al., "Overexpression of acid ceramidase (ASAH1) protects retinal cells (ARPE19) from oxidative stress", Journal of Lipid Research, vol. 60, pp. 30-43 (2019).
Suzuki, J., et al., "Cochlear gene therapy with ancestral AAV in adult mice: complete transduction of inner hair cells without cochlear dysfunction", Scientific Reports, 7:45524, pp. 1-11 (2017).
Youn, H., et al., "Modified mRNA as an alternative to plasmid DNA (pDNA) fortranscript replacement and vaccination therapy", Expert Opin. Biol. Ther., vol. 15, No. 9, pp. 1337-1348 (2015).
Zinn, E., et al., "In Silico Reconstruction of the Viral Evolutionary Lineage Yields a Potent Gene Therapy Vector", Cell Reports, vol. 12, pp. 1056-1068 (2015).
International Search Report and Written Opinion for International Application No. PCT/US2020/050411 (dated Dec. 17, 2020).
Kaur et al., "Modified mRNA as a Therapeutic Tool for the Heart," Cardiovascular Drugs and Therapy 34:871-880 (2020).
Magadum et al., "mRNA-Based Protein Replacement Therapy for the Heart," Molecular Therapy 27(4):785-93 (2019).
International Search Report and Written Opinion for International Application No. PCT/US2019/050634 (dated Dec. 13, 2019).
Chen et al., "The Sphingosine Kinase 1/Sphingosine-1-Phosphate Pathway in Pulmonary Arterial Hypertension," American Journal of Respiratory and Critical Care Medicine 190(9):1032-1043 (2014).
Gairhe et al., "Sphingosine-1-Phosphate is Involved in the Occlusive Arteriopathy of Pulmonary Arterial Hypertension," Pulmonary Circulation 6(3):369-380 (2016).
Pyne et al., "Sphingosine Kinase 1: A Potential Therapeutic Target in Pulmonary Arterial Hypertension?," Trends Mol. Med. 23:786-798 (2017).
Glogar et al., "Definition and Significance of the Area at Risk in Myocardial Infarct and the Ischemic Border Zone in Acute Myocardial Infarct," Acta Med. Austriaca Suppl. 36:1-40 (1986) (abstract only).
Zangi et al., "Modified mRNA Directs the Fate of Heart Progenitor Cells and Induces Vascular Regeneration After Myocardial Infarction," Nature Biotechnology 31:898 (2013).
Reforgiato et al., "Inhibition of Ceramide de Novo Synthesis as a Postischemic Strategy to Reduce Myocardial Reperfusion Injury," Basic Res. Cardiol. 111:12 (2016).
Supplementary European Search Report and Written Opinion for Application No. EP 19 76 3856 (dated Nov. 11, 2021).
Cannavo et al., "β1-Adrenergic Receptor and Sphingosine-1-Phosphate Receptor 1 (S1PR1) Reciprocal Downregulation Influences Cardiac Hypertrophic Response and Progression to Heart Failure: Protective Role of S1PR1 Cardiac Gene Therapy" Circulation, 2013, 128(15):1612-1622.
Gardlik et al., "Vectors and delivery systems in gene therapy," Medical Science Monitor, 2005, 11(4):RA110-121.
Koch et al., "Molecular Cloning and Characterization of a Full-length Complementary DNA Encoding Human Acid Ceramidase," The Journal of Biological Chemistry, 1996, 27(51):33110-33115.
Song et al., "Activation of PI3Kγ/Akt pathway increases cardiomyocyte HMGB1 expression in diabetic environment," Oncotarget, 2016, 7(49):80803-80810.
Sadowski et al., "The sequence-structure relationship and protein function prediction," Current Opinion in Structural Biology, 2009, 19:357-362.
Tang et al., "Identification of Dehalobacter reductive dehalogenases that catalyse dechlorination of chloroform 1,1,1-trichloroethane and 1,1-dichloroethane," Philosophical Transactions of the Royal Society B, 2013, 368(1616):20120318.
Houdebine, "The methods to generate transgenic animals and to control transgene expression," Journal of Biotechnology, 2002, 98:145-160.
Witkowski et al., "Conversion of a β-Ketoacyl Synthase to a Malonyl Decarboxylase by Replacement of the Active-Site Cysteine with Glutamine," Biochemistry, 1999, 38(36):11643-11650.
Seffernick et al., "Melamine Deaminase and Atrazine Chloroydrolase: 98 Percent Identical but Functionally Different," Journal of Bacteriology, 2001, 183(8):2405-2410.
Mullins et al., "Transgenesis in Nonmurine Species," Hypertension, 1993, 22(4):630-633.
Wang et al., "Delivery of CRISPR/CAS9 by Novel Strategies for Gene Therapy," Chembiochem, 2019, 20(5):634-643.
Phillips, "The challenge of gene therapy and DNA delivery," The Journal of Pharmacy and Pharmacology, 2001, 53(9):1169-1174.
Branden et al., "Prediction, Engineering, and Design of Protein Structures," Garland Publishing Inc., New York, 1991, 247.

\* cited by examiner

SEQUENCE LISTING

<160> NUMBER OF SEQ ID NOS: 34

<210> SEQ ID NO 1
<211> LENGTH: 1188
<212> TYPE: DNA
<213> ORGANISM: Artificial Sequence
<220> FEATURE:
<223> OTHER INFORMATION: synthetic vector

<400> SEQUENCE: 1

```
atgccgggcc ggagttgcgt cgccttagtc ctcctggctg ccgccgtcag ctgtgccgtc      60
gcgcagcacg cgccgccgtg gacagaggac tgcagaaaat caacctatcc tccttcagga     120
ccaacgtaca gaggtgcagt tccatggtac accataaatc ttgacttacc accctacaaa     180
agatggcatg aattgatgct tgacaaggca ccagtgctaa aggttatagt gaattctctg     240
aagaatatga taaatacatt cgtgccaagt ggaaaaatta tgcaggtggt ggatgaaaaa     300
ttgcctggcc tacttggcaa cttttcctggc cctttgaag aggaaatgaa gggtattgcc     360
gctgttactg atatacctt aggagagatt atttcattca atattttta tgaattattt      420 accatttgta cttcaatagt agcagaagac aaaaaaggtc atctaataca tgggagaaac     480
atggattttg gagtatttct tgggtggaac ataaataatg atacctgggt cataactgag     540
caactaaaac ctttaacagt gaatttggat ttccaaagaa acaacaaaac tgtcttcaag     600
gcttcaagct ttgctggcta tgtgggcatg ttaacaggat tcaaaccagg actgttcagt     660
cttacactga tgaacgtttt cagtataaat ggtggttatc tgggtattct agaatggatt     720
ctgggaaaga aagatgtcat gtggatagg ttcctcacta gaacagttct ggaaaatagc      780
acaagttatg aagaagccaa gaattatttg accaagacca agatattggc cccagcctac     840
tttatcctgg gaggcaacca gtctggggaa ggttgtgtga ttacacgaga cagaaaggaa     900
tcattggatg tatatgaact cgatgctaag cagggtagat ggtatgtggt acaaacaaat     960
tatgaccgtt ggaaacatcc cttcttcctt gatgatcgca gaacgcctgc aaagatgtgt    1020
ctgaaccgca ccagccaaga gaatatctca tttgaaacca tgtatgatgt cctgtcaaca    1080
aaacctgtcc tcaacaagct gaccgtatac acaaccttga tagatgttac caaaggtcaa    1140
ttcgaaactt acctgcggga ctgccctgac ccttgtatag gttggtga                 1188
```

<210> SEQ ID NO 2
<211> LENGTH: 1197
<212> TYPE: DNA
<213> ORGANISM: Artificial Sequence
<220> FEATURE:
<223> OTHER INFORMATION: synthetic oligomer

<400> SEQUENCE: 2

```
atggatccag tggtcggttg cggacgtggc ctctttggtt ttgttttctc agcgggcggc      60
ccccggggcg tgctcccgcg gccctgccgc gtgctggtgc tgctgaaccc gcgcggcggc     120
aagggcaagg ccttgcagct cttccggagt cacgtgcagc cccttttggc tgaggctgaa     180
atctccttca cgctgatgct cactgagcgg cggaaccacg cgcgggagct ggtgcggtcg     240
gaggagctgg gccgctggga cgctctggtg gtcatgtctg gagacgggct gatgcacgag     300
```

-continued

| | |
|---|---|
| gtggtgaacg ggctcatgga gcggcctgac tgggagaccg ccatccagaa gcccctgtgt | 360 |
| agcctcccag caggctctgg caacgcgctg gcagcttcct tgaaccatta tgctggctat | 420 |
| gagcaggtca ccaatgaaga cctcctgacc aactgcacgc tattgctgtg ccgccggctg | 480 |
| ctgtcaccca tgaacctgct gtctctgcac acggcttcgg ggctgcgcct cttctctgtg | 540 |
| ctcagcctgg cctggggctt cattgctgat gtggacctag agagtgagaa gtatcggcgt | 600 |
| ctgggggaga tgcgcttcac tctgggcacc ttcctgcgtc tggcagccct gcgcacctac | 660 |
| cgcggccgac tggcctacct ccctgtagga agagtgggtt ccaagacacc tgcctccccc | 720 |
| gttgtggtcc agcagggccc ggtagatgca caccttgtgc cactggagga gccagtgccc | 780 |
| tctcactgga cagtggtgcc cgacgaggac tttgtgctag tcctggcact gctgcactcg | 840 |
| cacctgggca gtgagatgtt tgctgcaccc atgggccgct gtgcagctgg cgtcatgcat | 900 |
| ctgttctacg tgcgggcggg agtgtctcgt gccatgctgc tgcgcctctt cctggccatg | 960 |
| gagaagggca ggcatatgga gtatgaatgc ccctacttgg tatatgtgcc cgtggtcgcc | 1020 |
| ttccgcttgg agcccaagga tgggaaaggt gtgtttgcag tggatgggga attgatggtt | 1080 |
| agcgaggccg tgcagggcca ggtgcacccca aactacttct ggatggtcag cggttgcgtg | 1140 |
| gagcccccgc ccagctggaa gccccagcag atgccaccgc cagaagagcc cttatga | 1197 |

<210> SEQ ID NO 3
<211> LENGTH: 1062
<212> TYPE: DNA
<213> ORGANISM: Artificial Sequence
<220> FEATURE:
<223> OTHER INFORMATION: synthetic oligomer

<400> SEQUENCE: 3

| | |
|---|---|
| atgggcagct tgtactcgga gtacctgaac cccaacaagg tccaggaaca ctataattat | 60 |
| accaaggaga cgctggaaac gcaggagacg acctcccgcc aggtggcctc ggccttcatc | 120 |
| gtcatcctct gttgcgccat tgtggtggaa aaccttctgg tgctcattgc ggtggcccga | 180 |
| aacagcaagt ccactcggc aatgtacctg tttctgggca acctggccgc ctccgatcta | 240 |
| ctggcaggcg tggccttcgt agccaatacc ttgctctctg gctctgtcac gctgaggctg | 300 |
| acgcctgtgc agtggtttgc ccgggagggc tctgccttca tcacgctctc ggcctctgtc | 360 |
| ttcagcctcc tggccatcgc cattgagcgc acgtgccca ttgccaaggt caagctgtat | 420 |
| ggcagcgaca gagctgccg catgcttctg ctcatcgggg cctcgtggct catctcgctg | 480 |
| gtcctcggtg gcctgcccat ccttggctgg aactgcctgg ccacctcga ggcctgctcc | 540 |
| actgtcctgc ctctctacgc caagcattat gtgctgtgcg tggtgaccat cttctccatc | 600 |
| atcctgttgg ccatcgtggc cctgtacgtg cgcatctact gcgtggtccg ctcaagccac | 660 |
| gctgacatgg ccgccccgca gacgctagcc ctgctcaaga cggtcaccat cgtgctaggc | 720 |
| gtctttatcg tctgctggct gccccgcctt c agcatcctcc ttctggacta tgcctgtccc | 780 |
| gtccactcct gcccgatcct ctacaaagcc cactactttt cgccgtctc cacccctgaat | 840 |
| tccctgctca accccgtcat ctacacgtgg cgcagccggg acctgcggcg ggaggtgctt | 900 |
| cggccgctgc agtgctggag gccggggtg ggggtgcaag gacggaggcg ggggcgggacc | 960 |
| ccgggccacc acctcctgcc actccgcagc tccagctccc tggagagggg catgcacatg | 1020 |
| cccacgtcac ccacgtttct ggagggcaac acggtggtca tg | 1062 |

<210> SEQ ID NO 4
<211> LENGTH: 1653

<212> TYPE: DNA
<213> ORGANISM: Artificial Sequence
<220> FEATURE:
<223> OTHER INFORMATION: synthetic oligomer

<400> SEQUENCE: 4

```
atggccgatg ctaagaacat taagaagggc cctgctccct tctaccctct ggaggatggc      60
accgctggcg agcagctgca caaggccatg aagaggtatg ccctggtgcc tggcaccatt     120
gccttcaccg atgcccacat tgaggtggac atcacctatg ccgagtactt cgagatgtct     180
gtgcgcctgg ccgaggccat gaagaggtac ggcctgaaca ccaaccaccg catcgtggtg     240
tgctctgaga actctctgca gttcttcatg ccagtgctgg gcgccctgtt catcggagtg     300
gccgtggccc tgctaacga catttacaac gagcgcgagc tgctgaacag catgggcatt     360
tctcagccta ccgtggtgtt cgtgtctaag aagggcctgc agaagatcct gaacgtgcag     420
aagaagctgc ctatcatcca gaagatcatc atcatggact ctaagaccga ctaccagggc     480
ttccagagca tgtacacatt cgtgacatct catctgcctc ctggcttcaa cgagtacgac     540
ttcgtgccag agtctttcga cagggacaaa accattgccc tgatcatgaa cagctctggg     600
tctaccggcc tgcctaaggg cgtggccctg cctcatcgca ccgcctgtgt gcgcttctct     660
cacgcccgcg acctatttt cggcaaccag atcatccccg acaccgctat tctgagcgtg     720
gtgccattcc accacggctt cggcatgttc accaccctgg ctacctgat tgcggctt     780
cgggtggtgc tgatgtaccg cttcgaggag gagctgttcc tgcgcagcct gcaagactac     840
aaaattcagt ctgccctgct ggtgccaacc ctgttcagct tcttcgctaa gagcaccctg     900
atcgacaagt acgacctgtc taacctgcac gagattgcct ctggcggcgc ccactgtct     960
aaggaggtgg cgaagccgt ggccaagcgc tttcatctgc caggcatccg ccagggctac    1020
ggcctgaccg agacaaccag cgccattctg attaccccag agggcgacga caagcctggc    1080
gccgtgggca aggtggtgcc attcttcgag gccaaggtgg tggacctgga caccggcaag    1140
accctgggag tgaaccagcg cggcgagctg tgtgtgcgcg ccctatgat tatgtccggc    1200
tacgtgaata cccctgaggc cacaaacgcc ctgatcgaca aggacggctg gctgcactct    1260
ggcgacattg cctactggga cgaggacgag cacttcttca tcgtggaccg cctgaagtct    1320
ctgatcaagt acaagggcta ccaggtggcc ccagccgagc tggagtctat cctgctgcag    1380
caccctaaca ttttcgacgc cggagtggcc ggcctgcccg acgacgatgc cggcgagctg    1440
cctgccgccg tcgtcgtgct ggaacacggc aagaccatga ccgagaagga gatcgtggac    1500
tatgtggcca gccaggtgac aaccgccaag aagctgcgcg cggagtggt gttcgtggac    1560
gaggtgccca agggcctgac cggcaagctg gacgcccgca agatccgcga gatcctgatc    1620
aaggctaaga aaggcggcaa gatcgccgtg taa                                 1653
```

<210> SEQ ID NO 5
<211> LENGTH: 801
<212> TYPE: DNA
<213> ORGANISM: Artificial Sequence
<220> FEATURE:
<223> OTHER INFORMATION: synthetic oligomer

<400> SEQUENCE: 5

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
```

| | |
|---|---|
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaaggga | 720 |
| gatccaaaaa agaagagaaa ggtaggcgat ccaaaaaaga gagaaaggt aggtgatcca | 780 |
| aaaaagaaga gaaaggtata a | 801 |

<210> SEQ ID NO 6
<211> LENGTH: 1236
<212> TYPE: DNA
<213> ORGANISM: Artificial Sequence
<220> FEATURE:
<223> OTHER INFORMATION: synthetic oligomer

<400> SEQUENCE: 6

| | |
|---|---|
| atgaactgct gcatcgggct gggagagaaa gctcgcgggt cccaccgggc ctcctaccca | 60 |
| agtctcagcg cgcttttcac cgaggcctca attctgggat ttggcagctt tgctgtgaaa | 120 |
| gcccaatgga cagaggactg cagaaaatca acctatcctc cttcaggacc aacgtacaga | 180 |
| ggtgcagttc catggtacac cataaatctt gacttaccac cctacaaaag atggcatgaa | 240 |
| ttgatgcttg acaaggcacc agtgctaaag gttatagtga attctctgaa gaatatgata | 300 |
| aatacattcg tgccaagtgg aaaaattatg caggtggtgg atgaaaaatt gcctggccta | 360 |
| cttggcaact tcctggcccc ttttgaagag gaaatgaagg gtattgccgc tgttactgat | 420 |
| atacctttag gagagattat ttcattcaat atttttttatg aattatttac catttgtact | 480 |
| tcaatagtag cagaagacaa aaaaggtcat ctaatacatg ggagaaacat ggattttgga | 540 |
| gtatttcttg ggtggaacat aaataatgat acctgggtca taactgagca actaaaacct | 600 |
| ttaacagtga atttggattt ccaaagaaac aacaaaactg tcttcaaggc ttcaagcttt | 660 |
| gctggctatg tgggcatgtt aacaggattc aaaccaggac tgttcagtct tacactgaat | 720 |
| gaacgtttca gtataaatgg tggttatctg ggtattctag aatggattct gggaaagaaa | 780 |
| gatgtcatgt ggatagggtt cctcactaga acagttctgg aaaatagcac aagttatgaa | 840 |
| gaagccaaga atttattgac caagaccaag atattggccc cagcctactt tatcctggga | 900 |
| ggcaaccagt ctggggaagg ttgtgtgatt acacgagaca gaaggaatc attggatgta | 960 |
| tatgaactcg atgctaagca gggtagatgg tatgtggtac aaacaaatta tgaccgttgg | 1020 |
| aaacatccct tcttccttga tgatcgcaga acgcctgcaa agatgtgtct gaaccgcacc | 1080 |
| agccaagaga atatctcatt tgaaaccatg tatgatgtcc tgtcaacaaa acctgtcctc | 1140 |
| aacaagctga ccgtatacac aaccttgata gatgttacca aaggtcaatt cgaaacttac | 1200 |
| ctgcgggact gccctgaccc ttgtataggt tggtga | 1236 |

<210> SEQ ID NO 7
<211> LENGTH: 1170
<212> TYPE: DNA
<213> ORGANISM: Artificial Sequence

```
<220> FEATURE:
<223> OTHER INFORMATION: synthetic oligomer

<400> SEQUENCE: 7
atgaactgct gcatcgggct gggagagaaa gctcgcgggt cccaccgggc ctcctaccca      60
agtctcagcg cgcttttcac cgaggcctca attctgggat ttggcagctt tgctgtgaaa     120
gcccaatgga cagaggactg cagaaaatca acctatcctc cttcaggacc aactgtcttc     180
cctgctgtta taaggtacag aggtgcagtt ccatggtaca ccataaatct tgacttacca     240
ccctacaaaa gatggcatga attgatgctt gacaaggcac cagtgcctgg cctacttggc     300
aactttcctg gccttttga agaggaaatg aagggtattg ccgctgttac tgatatacct      360
ttaggagaga ttatttcatt caatattttt tatgaattat ttaccatttg tacttcaata     420
gtagcagaag acaaaaaagg tcatctaata catgggagaa acatggattt tggagtattt     480
cttgggtgga acataaataa tgatacctgg gtcataactg agcaactaaa acctttaaca     540
gtgaatttgg attccaaag aaacaacaaa actgtcttca aggcttcaag ctttgctggc      600
tatgtgggca tgttaacagg attcaaacca ggactgttca gtcttacact gaatgaacgt     660
ttcagtataa atggtggtta tctgggtatt ctagaatgga ttctgggaaa gaaagatgtc     720
atgtggatag ggttcctcac tagaacagtt ctggaaaata gcacaagtta tgaagaagcc     780
aagaatttat tgaccaagac caagatattg gccccagcct actttatcct gggaggcaac     840
cagtctgggg aaggttgtgt gattacacga gacagaaagg aatcattgga tgtatatgaa     900
ctcgatgcta agcagggtag atggtatgtg gtacaaacaa attatgaccg ttggaaacat     960
cccttcttcc ttgatgatcg cagaacgcct gcaaagatgt gtctgaaccg caccagccaa    1020
gagaatatct catttgaaac catgtatgat gtcctgtcaa caaaacctgt cctcaacaag    1080
ctgaccgtat acacaacctt gatagatgtt accaaaggtc aattcgaaac ttacctgcgg    1140
gactgccctg acccttgtat aggttggtga                                     1170

<210> SEQ ID NO 8
<211> LENGTH: 2346
<212> TYPE: DNA
<213> ORGANISM: Artificial Sequence
<220> FEATURE:
<223> OTHER INFORMATION: synthetic oligomer

<400> SEQUENCE: 8
atggccaaac gcaccttctc taacttggag acattcctga ttttcctcct tgtaatgatg      60
agtgccatca cagtggccct tctcagcctc ttgtttatca ccagtgggac cattgaaaac     120
cacaaagatt taggaggcca tttttttttca accacccaaa gccctccagc cacccagggc    180
tccacagctg cccaacgctc cacagccacc cagcattcca cagccaccca gagctccaca     240
gccactcaaa cttctccagt gcctttaacc ccagagtctc ctctatttca gaacttcagt     300
ggctaccata ttggtgttgg acgagctgac tgcacaggac aagtagcaga tatcaatttg     360
atgggctatg gcaaatccgg ccagaatgca cagggcatcc tcaccaggct atacagtcgt     420
gccttcatca tggcagaacc tgatgggtcc aatcgaacag tgtttgtcag catcgacata     480
ggcatggtat cacaaaggct caggctggag gtcctgaaca gactgcagag taaatatggc     540
tccctgtaca agagagataa tgtcatcctg agtggcactc acactcattc aggtcctgca    600
ggatatttcc agtataccgt gtttgtaatt gccagtgaag gatttagcaa tcaaactttt    660
cagcacatgg tcactggtat cttgaagagc attgacatag cacacacaaa tatgaaacca    720
```

```
ggcaaaatct tcatcaataa aggaaatgtg gatggtgtgc agatcaacag aagtccgtat    780
tcttaccttc aaaatccgca gtcagagaga gcaaggtatt cttcaaatac agacaaggaa    840
atgatagttt tgaaaatggt agatttgaat ggagatgact tgggccttat cagctggttt    900
gccatccacc cggtcagcat gaacaacagt aaccatcttg taaacagtga caatgtgggc    960
tatgcatctt acctgcttga gcaagagaag aacaaaggat atctacctgg acaggggcca   1020
tttgtagcag cctttgcttc atcaaaccta ggagatgtgt cccccaacat tcttggacca   1080
cgttgcatca acacaggaga gtcctgtgat aacgccaata gcacttgtcc cattggtggg   1140
cctagcatgt gcattgctaa gggacctgga caggatatgt ttgacagcac acaaattata   1200
ggacgggcca tgtatcagag agcaaaggaa ctctatgcct ctgcctccca ggaggtaaca   1260
ggaccactgg cttcagcaca ccagtgggtg gatatgacag atgtgactgt ctggctcaat   1320
tccacacatg catcaaaaac atgtaaacca gcattgggct acagttttgc agctggcact   1380
attgatggag ttggaggcct caattttaca caggggaaaa cagaagggga tccattttgg   1440
gacaccattc gggaccagat cctgggaaag ccatctgaag aaattaaaga atgtcataaa   1500
ccaaagccca tccttcttca caccggagaa ctatcaaaac ctcacccctg gcatccagac   1560
attgttgatg ttcagattat tacccttggg tccttggcca taactgccat ccccggggag   1620
tttacgacca tgtctggacg aagacttcga gaggcagttc aagcagaatt tgcatctcat   1680
gggatgcaga acatgactgt tgttatttca ggtctatgca acgtctatac acattacatt   1740
accacttatg aagaatacca ggctcagcga tatgaggcag catcgacaat ttatggaccg   1800
cacacattat ctgcttacat tcagctcttc agaaaccttg ctaaggctat gctacggac   1860 acggtagcca acctgagcag aggtccagaa cctccctttt tcaaacaatt aatagttcca   1920
ttaattccta gtattgtgga tagagcacca aaaggcagaa ctttcgggga tgtcctgcag   1980
ccagcaaaac ctgaatacag agtggggaa gttgctgaag ttatatttgt aggtgctaac   2040
ccgaagaatt cagtacaaaa ccagacccat cagaccttcc tcactgtgga gaaatatgag   2100
gctacttcaa catcgtggca gatagtgtgt aatgatgcct cctgggagac tcgttttat    2160 tggcacaagg gactcctggg tctgagtaat gcaacagtgg aatggcatat tccagacact   2220
gcccagcctg gaatctacag aataagatat tttggacaca atcggaagca ggacattctg   2280
aagcctgctg tcatactttc atttgaaggc acttccccgg cttttgaagt tgtaactatt   2340
tagtga                                                              2346
```

<210> SEQ ID NO 9
<211> LENGTH: 2241
<212> TYPE: DNA
<213> ORGANISM: Artificial Sequence
<220> FEATURE:
<223> OTHER INFORMATION: synthetic oligomer

<400> SEQUENCE: 9

```
atggccaaac gcaccttctc taacttggag acattcctga ttttcctcct tgtaatgatg     60
agtgccatca cagtggccct tctcagcctc ttgtttatca ccagtgggac cattgaaaac    120
cacaaagatt taggaggcca tttttttca accacccaaa gccctccagc cacccagggc    180
tccacagctg cccaacgctc cacagccacc cagcattcca cagccaccca gagctccaca    240
gccactcaaa cttctccagt gccttaacc ccagagtctc ctctatttca gaacttcagt    300
ggctaccata ttggtgttgg acgagctgac tgcacaggac aagtagcaga tatcaatttg    360
atgggctatg caaatccgg ccagaatgca cagggcatcc tcaccaggct atacagtcgt    420
```

-continued

```
gccttcatca tggcagaacc tgatgggtcc aatcgaacag tgtttgtcag catcgacata    480
ggcatggtat cacaaaggct caggctggag gtcctgaaca gactgcagag taaatatggc    540
tccctgtaca gaagagataa tgtcatcctg agtggcactc acactcattc aggtcctgca    600
ggatatttcc agtataccgt gtttgtaatt gccagtgaag gatttagcaa tcaaactttt    660
cagcacatgg tcactggtat cttgaagagc attgacatag cacacacaaa tatgaaacca    720
ggcaaaatct tcatcaataa aggaaatgtg gatggtgtgc agatcaacag aagtccgtat    780
tcttaccttc aaaatccgca gtcagagaga gcaaggtatt cttcaaatac agacaaggaa    840
atgatagttt tgaaaatggt agatttgaat ggagatgact tgggccttat cagctggttt    900
gccatccacc cggtcagcat gaacaacagt aaccatcttg taaacagtga caatgtgggc    960
tatgcatctt acctgcttga gcaagagaag aacaaaggat atctacctgg acaggggcca   1020
tttgtagcag ccttttgcttc atcaaaccta ggagatgtgt cccccaacat tcttggacca   1080
cgttgcatca acacaggaga gtcctgtgat aacgccaata gcacttgtcc cattggtggg   1140
cctagcatgt gcattgctaa gggacctgga caggatatgt tgacagcac acaaattata   1200 ggacgggcca tgtatcagag agcaaagtca aaaacatgta aaccagcatt gggctacagt   1260
tttgcagctg gcactattga tggagttgga ggcctcaatt ttacacaggg gaaaacagaa   1320
ggggatccat tttgggacac cattcgggac cagatcctgg aaaagccatc tgaagaaatt   1380
aaagaatgtc ataaaccaaa gcccatcctt cttcacaccg gagaactatc aaaacctcac   1440
ccctggcatc cagacattgt tgatgttcag attattaccc ttgggtcctt ggccataact   1500
gccatccccg gggagtttac gaccatgtct ggacgaagac ttcgagaggc agttcaagca   1560
gaatttgcat ctcatgggat gcagaacatg actgttgtta tttcaggtct atgcaacgtc   1620
tatacacatt acattaccac ttatgaagaa taccaggctc agcgatatga ggcagcatcg   1680
acaatttatg gaccgcacac attatctgct tacattcagc tcttcagaaa ccttgctaag   1740
gctattgcta cggacacggt agccaacctg agcagaggtc cagaacctcc cttttttcaaa  1800 caattaatag ttccattaat tcctagtatt gtggatagag caccaaaagg cagaactttc   1860
ggggatgtcc tgcagccagc aaaacctgaa tacagagtgg gggaagttgc tgaagttata   1920
tttgtaggtg ctaacccgaa gaattcagta caaaaccaga cccatcagac cttcctcact   1980
gtggagaaat atgaggctac ttcaacatcg tggcagatag tgtgtaatga tgcctcctgg   2040
gagactcgtt tttattggca caagggactc ctgggtctga gtaatgcaac agtggaatgg   2100
catattccag acactgccca gcctggaatc tacagaataa gatattttgg acacaatcgg   2160
aagcaggaca ttctgaagcc tgctgtcata ctttcatttg aaggcacttc cccggctttt   2220
gaagttgtaa ctatttagtg a                                              2241
```

<210> SEQ ID NO 10
<211> LENGTH: 501
<212> TYPE: DNA
<213> ORGANISM: Artificial Sequence
<220> FEATURE:
<223> OTHER INFORMATION: synthetic oligomer

<400> SEQUENCE: 10

```
atgaggcagc atcgacaatt tatggaccgc acgcattatc tgcttacatt cagctcttca    60
gaaaccttgc taaggctatt gctacgtatt gtggatagag caccaaaagg cagaactttc   120
ggggatgtcc tgcagccagc aaaacctgaa tacagagtgg gggaagttgc tgaagttata   180
```

| | |
|---|---|
| tttgtaggtg ctaacccgaa gaattcagta caaaaccaga cccatcagac cttcctcact | 240 |
| gtggagaaat atgaggctac ttcaacatcg tggcagatag tgtgtaatga tgcctcctgg | 300 |
| gagactcgtt tttattggca caagggactc ctgggtctga gtaatgcaac agtggaatgg | 360 |
| catattccag acactgccca gcctggaatc tacagaataa gatattttgg acacaatcgg | 420 |
| aagcaggaca ttctgaagcc tgctgtcata ctttcatttg aaggcacttc cccggctttt | 480 |
| gaagttgtaa ctatttagtg a | 501 |

<210> SEQ ID NO 11
<211> LENGTH: 972
<212> TYPE: DNA
<213> ORGANISM: Artificial Sequence
<220> FEATURE:
<223> OTHER INFORMATION: synthetic oligomer

<400> SEQUENCE: 11

| | |
|---|---|
| atggtagcca acctgagcag aggtccagaa cctcccttt tcaaacaatt aatagttcca | 60 |
| ttaattccta gtattgtgga tagagcacca aaaggcagaa ctttcgggga tgtcctgcag | 120 |
| ccagcaaaac ctgaatacag agtgggggaa gttgctgaag ttatatttgt aggtgctaac | 180 |
| ccgaagaatt cagtacaaaa ccagacccat cagaccttcc tcactgtgga gaaatatgag | 240 |
| gctacttcaa catcgtggca gatagtgtgt aatgatgcct cctgggagac tcgttttat | 300 |
| tggcacaagg gactcctggg tctgagtaat gcaacagtgg aatggcatat tccagacact | 360 |
| gcccagcctg gaatctacag aataagatat tttggacaca atcggaagca ggacattctg | 420 |
| aagcctgctg tcatactttc atttgaaggc acttccccgg cttttgaagt tgtaactatt | 480 |
| tagtgaatgg tagccaacct gagcagaggt ccagaacctc cttttcaa acaattaata | 540 |
| gttccattaa ttcctagtat tgtggataga gcaccaaaag gcagaacttt cggggatgtc | 600 |
| ctgcagccag caaaacctga atacagagtg ggggaagttg ctgaagttat atttgtaggt | 660 |
| gctaacccga gaattcagt acaaaaccag acccatcaga ccttcctcac tgtggagaaa | 720 |
| tatgaggcta cttcaacatc gtggcagata gtgtgtaatg atgcctcctg ggagactcgt | 780 |
| ttttattggc acaagggact cctgggtctg agtaatgcaa cagtggaatg gcatattcca | 840 |
| gacactgccc agcctggaat ctacagaata agatattttg gacacaatcg gaagcaggac | 900 |
| attctgaagc tgctgtcat actttcattt gaaggcactt ccccggcttt tgaagttgta | 960 |
| actatttagt ga | 972 |

<210> SEQ ID NO 12
<211> LENGTH: 483
<212> TYPE: DNA
<213> ORGANISM: Artificial Sequence
<220> FEATURE:
<223> OTHER INFORMATION: synthetic oligomer

<400> SEQUENCE: 12

| | |
|---|---|
| atggtagcca acctgagcag aggtccagaa cctcccttt tcaaacaatt aatagttcca | 60 |
| ttaattccta gtattgtgga tagagcacca aaaggcagaa ctttcgggga tgtcctgcag | 120 |
| ccagcaaaac ctgaatacag agtgggggaa gttgctgaag ttatatttgt aggtgctaac | 180 |
| ccgaagaatt cagtacaaaa ccagacccat cagaccttcc tcactgtgga gaaatatgag | 240 |
| gctacttcaa catcgtggca gatagtgtgt aatgatgcct cctgggagac tcgttttat | 300 |
| tggcacaagg gactcctggg tctgagtaat gcaacagtgg aatggcatat tccagacact | 360 |

```
gcccagcctg gaatctacag aataagatat tttggacaca atcggaagca ggacattctg    420
aagcctgctg tcatactttc atttgaaggc acttccccgg cttttgaagt tgtaactatt    480
tag                                                                  483
```

<210> SEQ ID NO 13
<211> LENGTH: 795
<212> TYPE: DNA
<213> ORGANISM: Artificial Sequence
<220> FEATURE:
<223> OTHER INFORMATION: synthetic oligomer

<400> SEQUENCE: 13

```
atgcctagca tcttcgccta tcagagctcc gaggtggact ggtgtgagag caacttccag     60
tactcggagc tggtggccga gttctacaac acgttctcca atatcccctt cttcatcttc    120
gggccactga tgatgctcct gatgcacccg tatgcccaga gcgctcccg ctacatttac     180 gttgtctggg tcctcttcat gatcataggc ctgttctcca tgtatttcca catgacgctc    240
agcttcctgg ccagctgct ggacgagatc gccatcctgt ggctcctggg cagtggctat     300
agcatatgga tgccccgctg ctatttcccc tccttccttg gggggaacag gtcccagttc    360
atccgcctgg tcttcatcac cactgtggtc agcacccttc tgtccttcct gcggcccacg    420
gtcaacgcct acgccctcaa cagcattgcc ctgcacattc tctacatcgt gtgccaggag    480
tacaggaaga ccagcaataa ggagcttcgg cacctgattg aggtctccgt ggttttatgg    540
gctgttgctc tgaccagctg gatcagtgac cgtctgcttt gcagcttctg gcagaggatt    600
catttcttct atctgcacag catctggcat gtgctcatca gcatcacctt cccttatggc    660
atggtcacca tggccttggt ggatgccaac tatgagatgc aggtgaaaac cctcaaagtc    720
cgctactggc tcgggacag ttggcccgtg gggctgccct acgtggaaat ccggggtgat    780
gacaaggact gctga                                                    795
```

<210> SEQ ID NO 14
<211> LENGTH: 828
<212> TYPE: DNA
<213> ORGANISM: Artificial Sequence
<220> FEATURE:
<223> OTHER INFORMATION: synthetic oligomer

<400> SEQUENCE: 14

```
atgggcgccc cgcactggtg ggaccagctg caggctggta gctcggaggt ggactggtgc     60
gaggacaact acaccatcgt gcctgctatc gccgagttct acaacacgat cagcaatgtc    120
ttatttttca ttttaccgcc catctgcatg tgcttgtttc gtcagtatgc aacatgcttc    180
aacagtggca tctacttaat ctggactctt ttggttgtag tgggaattgg atccgtctac    240
ttccatgcaa cccttagttt cttgggtcag atgcttgatg aacttgcagt cctttgggtt    300
ctgatgtgtg ctttggccat gtggttcccc agaaggtatc taccaaagat ctttcggaat    360
gaccggggta ggttcaaggt ggtggtcagt gtcctgtctg cggttacgac gtgcctggca    420
tttgtcaagc ctgccatcaa caacatctct ctgatgaccc tgggagttcc ttgcactgca    480
ctgctcatcg cagagctaaa gaggtgtgac aacatgcgtg tgtttaagct gggcctcttc    540
tcgggcctct ggtggaccct ggccctgttc tgctggatca gtgaccgagc tttctgcgag    600
ctgctgtcat cctcaacttt cccctacctg cactgcatgt ggcacatcct catctgcctt    660
gctgcctacc tgggctgtgt atgctttgcc tactttgatg ctgcctcaga gattcctgag    720
```

| caaggccctg tcatcaagtt ctggcccaat gagaaatggg ccttcattgg tgtcccctat | 780 |
| gtgtccctcc tgtgtgccaa caagaaatca tcagtcaaga tcacgtga | 828 |

<210> SEQ ID NO 15
<211> LENGTH: 804
<212> TYPE: DNA
<213> ORGANISM: Artificial Sequence
<220> FEATURE:
<223> OTHER INFORMATION: synthetic oligomer

<400> SEQUENCE: 15

| atggctccgg ccgcggaccg agagggctac tggggcccca cgacctccac gctggactgg | 60 |
| tgcgaggaga actactccgt gacctggtac atcgccgagt tctggaatac agtgagtaac | 120 |
| ctgatcatga ttatacctcc aatgttcggt gcagttcaga gtgttagaga cggtctggaa | 180 |
| aagcggtaca ttgcttctta tttagcactc acagtggtag aatgggatc ctggtgcttc | 240 |
| cacatgactc tgaaatatga atgcagcta ttggatgaac tcccaatgat atacagctgt | 300 |
| tgcatatttg tgtactgcat gtttgaatgt ttcaagatca agaactcagt aaactaccat | 360 |
| ctgcttttta ccttagttct attcagttta atagtaacca cagtttacct taaggtaaaa | 420 |
| gagccgatat tccatcaggt catgtatgga atgttggtct ttacattagt acttcgatct | 480 |
| atttatattg ttacatgggt ttatccatgg cttagaggac tgggttatac atcattgggt | 540 |
| atatttttat tgggattttt attttggaat atagataaca tattttgtga gtcactgagg | 600 |
| aactttcgaa agaaggtacc acctatcata ggtattacca cacaatttca tgcatggtgg | 660 |
| catatttaa ctggccttgg ttcctatctt cacatccttt tcagtttgta tacaagaaca | 720 |
| ctttacctga gatataggcc aaaagtgaag tttctctttg gaatctggcc agtgatcctg | 780 |
| tttgagcctc tcaggaagca ttga | 804 |

<210> SEQ ID NO 16
<211> LENGTH: 693
<212> TYPE: DNA
<213> ORGANISM: Artificial Sequence
<220> FEATURE:
<223> OTHER INFORMATION: synthetic oligomer

<400> SEQUENCE: 16

| atggctccgg ccgcggaccg agagggctac tggggcccca cgacctccac gctggactgg | 60 |
| tgcgaggaga actactccgt gacctggtac atcgccgagt tcttggtagg aatgggatcc | 120 |
| tggtgcttcc acatgactct gaaatatgaa atgcagctat ggatgaact cccaatgata | 180 |
| tacagctgtt gcatatttgt gtactgcatg tttgaatgtt tcaagatcaa gaactcagta | 240 |
| aactaccatc tgcttttac cttagttcta ttcagtttaa tagtaaccac agtttacctt | 300 |
| aaggtaaaag agccgatatt ccatcaggtc atgtatggaa tgttggtctt tacattagta | 360 |
| cttcgatcta tttatattgt tacatgggtt tatccatggc ttagaggact gggttataca | 420 |
| tcattgggta tattttatt gggatttta ttttggaata tagataacat attttgtgag | 480 |
| tcactgagga actttcgaaa gaaggtacca cctatcatag gtattaccac acaatttcat | 540 |
| gcatggtggc atattttaac tggccttggt tcctatcttc acatcctttt cagtttgtat | 600 |
| acaagaacac tttacctgag atataggcca aaagtgaagt ttctctttgg aatctggcca | 660 |
| gtgatcctgt ttgagcctct caggaagcat tga | 693 |

<210> SEQ ID NO 17
<211> LENGTH: 519

| | |
|---|---|
| <212> TYPE: DNA | |
| <213> ORGANISM: Artificial Sequence | |
| <220> FEATURE: | |
| <223> OTHER INFORMATION: synthetic oligomer | |

<400> SEQUENCE: 17

| | |
|---|---|
| atgatataca gctgttgcat atttgtgtac tgcatgtttg aatgtttcaa gatcaagaac | 60 |
| tcagtaaaact accatctgct ttttaccttaa gttctattca gtttaatagt aaccacagtt | 120 |
| taccttaagg taaaagagcc gatattccat caggtcatgt atggaatgtt ggtctttaca | 180 |
| ttagtacttc gatctattta tattgttaca tgggtttatc catggcttag aggactgggt | 240 |
| tatacatcat tgggtatatt ttttattgga ttttttatttt ggaatataga taacatattt | 300 |
| tgtgagtcac tgaggaactt tcgaaagaag gtaccaccta tcataggtat taccacacaa | 360 |
| tttcatgcat ggtggcatat tttaactggc cttggttcct atcttcacat ccttttcagt | 420 |
| ttgtatacaa gaacacttta cctgagatat aggccaaaag tgaagtttct ctttggaatc | 480 |
| tggccagtga tcctgtttga gcctctcagg aagcattga | 519 |

| | |
|---|---|
| <210> SEQ ID NO 18 | |
| <211> LENGTH: 1965 | |
| <212> TYPE: DNA | |
| <213> ORGANISM: Artificial Sequence | |
| <220> FEATURE: | |
| <223> OTHER INFORMATION: synthetic oligomer | |

<400> SEQUENCE: 18

| | |
|---|---|
| atgaatggac accttgaagc agaggagcag caggaccaga ggccagacca ggagctgacc | 60 |
| gggagctggg gccacgggcc taggagcacc ctggtcaggg ctaaggccat ggccccgccc | 120 |
| ccaccgccac tggctgccag caccccgctc ctccatggcg agtttggctc ctacccagcc | 180 |
| cgaggcccac gctttgccct caccctaaca tcgcaggccc tgcacataca gcggctgcgc | 240 |
| cccaaacctg aagccaggcc ccggggtggc ctggtcccgt tggccgaggt ctcaggctgc | 300 |
| tgcaccctgc gaagccgcag ccctcagac tcagcggcct acttctgcat ctacacctac | 360 |
| cctcggggcc ggcgcgggc ccggcgcaga gccactcgca ccttccgggc agatggggcc | 420 |
| gccacctacg aagagaaccg tgccgaggcc cagcgctggg ccactgccct cacctgtctg | 480 |
| ctccgaggac tgccactgcc cggggatggg gagatcaccc ctgacctgct acctcggccg | 540 |
| ccccggttgc ttctattggt caatcccttt ggggtcggg gcctggcctg gcagtggtgt | 600 |
| aagaaccacg tgcttcccat gatctctgaa gctgggctgt ccttcaacct catccagaca | 660 |
| gaacgacaga accacgcccg ggagctggtc caggggctga gctgagtga gtgggatggc | 720 |
| atcgtcacgg tctcgggaga cgggctgctc catgaggtgc tgaacgggct cctagatcgc | 780 |
| cctgactggg aggaagctgt gaagatgcct gtgggcatcc tcccctgcgg ctcgggcaac | 840 |
| gcgctggccg gagcagtgaa ccagcacggg ggatttgagc cagccctggg cctcgacctg | 900 |
| ttgctcaact gctcactgtt gctgtgccgg ggtggtggcc acccactgga cctgctctcc | 960 |
| gtgacgctgg cctcgggctc ccgctgtttc tccttcctgt ctgtggcctg ggcttcgtg | 1020 |
| tcagatgtgg atatccagag cgagcgcttc agggccttgg gcagtgcccg cttcacactg | 1080 |
| ggcacggtgc tgggcctcgc cacactgcac acctaccgcg gacgcctctc ctacctcccc | 1140 |
| gccactgtgg aacctgcctc gcccaccccct gccatagcc tgcctcgtgc caagtcggag | 1200 |
| ctgacccctaa ccccagaccc agcccgcccc atgcccact caccccctgca tcgttctgtg | 1260 |
| tctgacctgc ctcttccccct gccccagcct gccctggcct ctcctggctc gccagaaccc | 1320 |

| | | |
|---|---|---|
| ctgcccatcc tgtccctcaa cggtgggggc ccagagctgg ctggggactg ggtgggggct | 1380 | |
| ggggatgctc cgctgtcccc ggacccactg ctgtcttcac ctcctggctc tcccaaggca | 1440 | |
| gctctacact cacccgtctc cgaaggggcc cccgtaattc ccccatcctc tgggctccca | 1500 | |
| cttcccaccc ctgatgcccg ggtaggggcc tccacctgcg gcccgcccga ccacctgctg | 1560 | |
| cctccgctgg gcacccgct gccccagac tgggtgacgc tggaggggga ctttgtgctc | 1620 | |
| atgttggcca tctcgcccag ccacctaggc gctgacctgg tggcagctcc gcatgcgcgc | 1680 | |
| ttcgacgacg gcctggtgca cctgtgctgg gtgcgtagcg gcatctcgcg ggctgcgctg | 1740 | |
| ctgcgccttt tcttggccat ggagcgtggt agccacttca gcctgggctg tccgcagctg | 1800 | |
| ggctacgccg cggcccgtgc cttccgccta gagccgctca caccacgcgg cgtgctcaca | 1860 | |
| gtggacgggg agcaggtgga gtatgggccg ctacaggcac agatgcaccc tggcatcggt | 1920 | |
| acactgctca ctgggcctcc tggctgcccg gggcgggagc cctga | 1965 | |

<210> SEQ ID NO 19
<211> LENGTH: 1614
<212> TYPE: DNA
<213> ORGANISM: Artificial Sequence
<220> FEATURE:
<223> OTHER INFORMATION: synthetic oligomer

<400> SEQUENCE: 19

| | | |
|---|---|---|
| atggggggcga cggggggcggc ggagccgctg caatccgtgc tgtgggtgaa gcagcagcgc | 60 | |
| tgcgccgtga gcctggagcc cgcgcgggct ctgctgcgct ggtggcggag cccggggccc | 120 | |
| ggagccggcg ccccggcgc ggatgcctgc tctgtgcctg tatctgagat catcgccgtt | 180 | |
| gaggaaacag acgttcacgg gaaacatcaa ggcagtggaa aatggcagaa aatggaaaag | 240 | |
| ccttacgctt ttacagttca ctgtgtaaag agagcacgac ggcaccgctg gaagtgggcg | 300 | |
| caggtgactt tctggtgtcc agaggagcag ctgtgtcact tgtggctgca gaccctgcgg | 360 | |
| gagatgctgg agaagctgac gtccagacca aagcatttac tggtatttat caacccgttt | 420 | |
| ggaggaaaag gacaaggcaa gcggatatat gaaagaaaag tggcaccact gttcacctta | 480 | |
| gcctccatca ccactgacat catcgttact gaacatgcta atcaggccaa ggagactctg | 540 | |
| tatgagatta acatagacaa atacgacggc atcgtctgtg tcggcggaga tggtatgttc | 600 | |
| agcgaggtgc tgcacggtct gattgggagg acgcagagga gcgccggggt cgaccagaac | 660 | |
| caccccgggg ctgtgctggt ccccagtagc ctccggattg aatcattccc gcagggtca | 720 | |
| acggactgcg tgtgttactc caccgtgggc accagcgacg cagaaacctc ggcgctgcat | 780 | |
| atcgttgttg gggactcgct ggccatggat gtgtcctcag tccaccacaa cagcacactc | 840 | |
| cttcgctact ccgtgtccct gctgggctac ggcttctacg gggacatcat caaggacagt | 900 | |
| gagaagaaac ggtggttggg tcttgccaga tacgactttt caggtttaaa gaccttcctc | 960 | |
| tcccaccact gctatgaagg gacagtgtcc ttcctccctg cacaacacac ggtgggatct | 1020 | |
| ccaagggata ggaagccctg ccgggcagga tgctttgttt gcaggcaaag caagcagcag | 1080 | |
| ctggaggagg agcagaagaa agcactgtat ggtttggaag ctgcggagga cgtggaggag | 1140 | |
| tggcaagtcg tctgtgggaa gtttctggcc atcaatgcca caacatgtc ctgtgcttgt | 1200 | |
| cgccggagcc ccaggggcct ctccccggct gcccacttgg gagacgggtc ttctgacctc | 1260 | |
| atcctcatcc ggaaatgctc caggttcaat tttctgagat ttctcatcag gcacaccaac | 1320 | |
| cagcaggacc agtttgactt cacttttgtt gaagtttatc gcgtcaagaa attccagttt | 1380 | |
| acgtcgaagc acatggagga tgaggacagc gacctcaagg agggggggaa gaagcgcttt | 1440 | |

-continued

```
gggcacattt gcagcagcca cccctcctgc tgctgcaccg tctccaacag ctcctggaac    1500
tgcgacgggg aggtcctgca cagccctgcc atcgaggtca gagtccactg ccagctggtt    1560
cgactctttg cacgaggaat tgaagagaat ccgaagccag actcacacag ctga          1614
```

<210> SEQ ID NO 20
<211> LENGTH: 4779
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (980)..(982)
<223> OTHER INFORMATION: n is a, c, g, or t

<400> SEQUENCE: 20

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagc tagttattaa tagtaatcaa ttacggggtc    240
attagttcat agcccatata tggagttccg cgttacataa cttacggtaa atggcccgcc    300
tggctgaccg cccaacgacc cccgcccatt gacgtcaata atgacgtatg ttcccatagt    360
aacgccaata gggactttcc attgacgtca atgggtggag tatttacggt aaactgccca    420
cttggcagta catcaagtgt atcatatgcc aagtacgccc cctattgacg tcaatgacgg    480
taaatggccc gcctggcatt atgcccagta catgacctta tgggactttc ctacttggca    540
gtacatctac gtattagtca tcgctattac catggtgatg cggttttggc agtacatcaa    600
tgggcgtgga tagcggtttg actcacgggg atttccaagt ctccacccca ttgacgtcaa    660
tgggagtttg ttttggcacc aaaatcaacg ggactttcca aaatgtcgta acaactccgc    720
cccattgacg caaatgggcg gtaggcgtgt acggtgggag gtctatataa gcagagctgg    780
tttagtgaac cgtcagatcc tgcagaagtt ggtcgtgagg cactgggcag gtaagtatca    840
aggttacaag acaggtttaa ggagaccaat agaaactggg cttgtcgaga cagagaagac    900
tcttgcgttt ctgataggca cctattggtc ttactgacat ccactttgcc tttctctcca    960
caggtgtcca ggcggccgcn nnggatccaa tcaacctctg gattacaaaa tttgtgaaag   1020
attgactggt attcttaact atgttgctcc ttttacgcta tgtggatacg ctgctttaat   1080
gcctttgtat catgctattg cttcccgtat ggctttcatt ttctcctcct tgtataaatc   1140
ctggttgctg tctctttatg aggagttgtg gcccgttgtc aggcaacgtg gcgtggtgtg   1200
cactgtgttt gctgacgcaa cccccactgg ttggggcatt gccaccacct gtcagctcct   1260
ttccgggact ttcgctttcc ccctcccatt gccacggcg gaactcatcg ccgcctgcct   1320
tgcccgctgc tggacagggg ctcggctgtt gggcactgac aattccgtgg tgttgtcggg   1380
gaaatcatcg tcctttcctt ggctgctcgc ctgtgttgcc acctggattc tgcgcgggac   1440
gtccttctgc tacgtccctt cggccctcaa tccagcggac cttccttccc gcggcctgct   1500
gccggctctg cggcctcttc cgcgtcttcg agatctgcct cgactgtgcc ttctagttgc   1560
cagccatctg ttgtttgccc ctcccccgtg ccttccttga ccctggaagg tgccactccc   1620
actgtccttt cctaataaaa tgaggaaatt gcatcgcatt gtctgagtag gtgtcattct   1680
attctggggg gtggggtggg gcaggacagc aaggggggagg attgggaaga caatagcagg   1740
```

-continued

```
catgctgggg actcgagtta agggcgaatt cccgataagg atcttcctag agcatggcta    1800
cgtagataag tagcatggcg ggttaatcat taactacaag gaacccctag tgatggagtt    1860
ggccactccc tctctgcgcg ctcgctcgct cactgaggcc gggcgaccaa aggtcgcccg    1920
acgcccgggg tttgcccggg cggcctcagt gagcgagcga gcgcgcagcc ttaattaacc    1980
taattcactg gccgtcgttt tacaacgtcg tgactgggaa aaccctggcg ttacccaact    2040
taatcgcctt gcagcacatc cccctttcgc cagctggcgt aatagcgaag aggcccgcac    2100
cgatcgccct tcccaacagt tgcgcagcct gaatggcgaa tgggacgcgc cctgtagcgg    2160
cgcattaagc gcggcgggtg tggtggttac gcgcagcgtg accgctacac ttgccagcgc    2220
cctagcgccc gctcctttcg ctttcttccc ttcctttctc gccacgttcg ccggctttcc    2280
ccgtcaagct ctaaatcggg ggctcccttt agggttccga tttagtgctt tacggcacct    2340
cgaccccaaa aaacttgatt agggtgatgg ttcacgtagt gggccatcgc cctgatagac    2400
ggtttttcgc cctttgacgt tggagtccac gttctttaat agtggactct tgttccaaac    2460
tggaacaaca ctcaacccta tctcggtcta ttcttttgat ttataaggga ttttgccgat    2520
ttcggcctat tggttaaaaa atgagctgat ttaacaaaaa tttaacgcga attttaacaa    2580
aatattaacg tttataattt caggtggcat cttttcgggga aatgtgcgcg aacccctat    2640 ttgtttattt ttctaaatac attcaaatat gtatccgctc atgagacaat aaccctgata    2700
aatgcttcaa taatattgaa aaaggaagag tatgagtatt caacatttcc gtgtcgccct    2760
tattcccttt tttgcggcat tttgccttcc tgttttgct cacccagaaa cgctggtgaa    2820
agtaaaagat gctgaagatc agttgggtgc acgagtgggt tacatcgaac tggatctcaa    2880
tagtggtaag atccttgaga gttttcgccc cgaagaacgt tttccaatga tgagcacttt    2940
taaagttctg ctatgtggcg cggtattatc ccgtattgac gccgggcaag agcaactcgg    3000
tcgccgcata cactattctc agaatgactt ggttgagtac tcaccagtca cagaaaagca    3060
tcttacggat ggcatgacag taagagaatt atgcagtgct gccataacca tgagtgataa    3120
cactgcggcc aacttacttc tgacaacgat cggaggaccg aaggagctaa ccgcttttt    3180 gcacaacatg ggggatcatg taactcgcct tgatcgttgg gaaccggagc tgaatgaagc    3240
cataccaaac gacgagcgtg acaccacgat gcctgtagta atggtaacaa cgttgcgcaa    3300
actattaact ggcgaactac ttactctagc ttcccggcaa caattaatag actggatgga    3360
ggcggataaa gttgcaggac cacttctgcg ctcggccctt ccggctggct ggtttattgc    3420
tgataaatct ggagccggtg agcgtgggtc tcgcggtatc attgcagcac tggggccaga    3480
tggtaagccc tcccgtatcg tagttatcta cacgacgggg agtcaggcaa ctatggatga    3540
acgaaataga cagatcgctg agataggtgc ctcactgatt aagcattggt aactgtcaga    3600
ccaagtttac tcatatatac tttagattga tttaaaactt catttttaat ttaaaaggat    3660
ctaggtgaag atcctttttg ataatctcat gaccaaaatc ccttaacgtg agttttcgtt    3720
ccactgagcg tcagaccccg tagaaaagat caaaggatct tcttgagatc ctttttttct    3780
gcgcgtaatc tgctgcttgc aaacaaaaaa accaccgcta ccagcggtgg tttgtttgcc    3840
ggatcaagag ctaccaactc tttttccgaa ggtaactggc ttcagcagag cgcagatacc    3900
aaatactgtc cttctagtgt agccgtagtt aggccaccac ttcaagaact ctgtagcacc    3960
gcctacatac ctcgctctgc taatcctgtt accagtggct gctgccagtg gcgataagtc    4020
gtgtcttacc gggttggact caagacgata gttaccggat aaggcgcagc ggtcgggctg    4080
aacggggggt tcgtgcacac agcccagctt ggagcgaacg acctacaccg aactgagata    4140
```
cctacagcgt gagctatgag aaagcgccac gcttcccgaa gggagaaagg cggacaggta    4200
tccggtaagc ggcagggtcg gaacaggaga gcgcacgagg gagcttccag ggggaaacgc    4260
ctggtatctt tatagtcctg tcgggtttcg ccacctctga cttgagcgtc gattttgtg    4320 atgctcgtca gggggggcgga gcctatggaa aaacgccagc aacgcggcct ttttacggtt    4380
cctggccttt tgctgcggtt ttgctcacat gttctttcct gcgttatccc ctgattctgt    4440
ggataaccgt attaccgcct ttgagtgagc tgataccgct cgccgcagcc gaacgaccga    4500
gcgcagcgag tcagtgagcg aggaagcgga agagcgccca atacgcaaac cgcctctccc    4560
cgcgcgttgg ccgattcatt aatgcagctg gcacgacagg tttcccgact ggaaagcggg    4620
cagtgagcgc aacgcaatta atgtgagtta gctcactcat taggcacccc aggctttaca    4680
ctttatgctt ccggctcgta tgttgtgtgg aattgtgagc ggataacaat ttcacacagg    4740
aaacagctat gaccatgatt acgccagatt taattaagg                            4779

<210> SEQ ID NO 21
<211> LENGTH: 22
<212> TYPE: DNA
<213> ORGANISM: Artificial Sequence
<220> FEATURE:
<223> OTHER INFORMATION: synthetic oligo

<400> SEQUENCE: 21
acaggattca aaccaggact gt                                              22

<210> SEQ ID NO 22
<211> LENGTH: 20
<212> TYPE: DNA
<213> ORGANISM: Artificial Sequence
<220> FEATURE:
<223> OTHER INFORMATION: synthetic oligo

<400> SEQUENCE: 22
tgggcatctt tccttccgaa                                                 20

<210> SEQ ID NO 23
<211> LENGTH: 22
<212> TYPE: DNA
<213> ORGANISM: Artificial Sequence
<220> FEATURE:
<223> OTHER INFORMATION: synthetic oligo

<400> SEQUENCE: 23
tgacaggatt caaaccagga ct                                              22

<210> SEQ ID NO 24
<211> LENGTH: 20
<212> TYPE: DNA
<213> ORGANISM: Artificial Sequence
<220> FEATURE:
<223> OTHER INFORMATION: synthetic oligo

<400> SEQUENCE: 24
ctgggcatct ttccttccga                                                 20

<210> SEQ ID NO 25
<211> LENGTH: 22
<212> TYPE: DNA
<213> ORGANISM: Artificial Sequence
<220> FEATURE:
<223> OTHER INFORMATION: synthetic oligo

```
<400> SEQUENCE: 25
atactcaccg aacggaagaa cc                                              22

<210> SEQ ID NO 26
<211> LENGTH: 22
<212> TYPE: DNA
<213> ORGANISM: Artificial Sequence
<220> FEATURE:
<223> OTHER INFORMATION: synthetic oligo

<400> SEQUENCE: 26
ccattagccc attcaccacc tc                                              22

<210> SEQ ID NO 27
<211> LENGTH: 21
<212> TYPE: DNA
<213> ORGANISM: Artificial Sequence
<220> FEATURE:
<223> OTHER INFORMATION: synthetic oligo

<400> SEQUENCE: 27
actgatactc accgaacgga a                                               21

<210> SEQ ID NO 28
<211> LENGTH: 21
<212> TYPE: DNA
<213> ORGANISM: Artificial Sequence
<220> FEATURE:
<223> OTHER INFORMATION: synthetic oligo

<400> SEQUENCE: 28
cattagccca ttcaccacct c                                               21

<210> SEQ ID NO 29
<211> LENGTH: 20
<212> TYPE: DNA
<213> ORGANISM: Artificial Sequence
<220> FEATURE:
<223> OTHER INFORMATION: synthetic oligo

<400> SEQUENCE: 29
cacagccaac agtctccaaa                                                 20

<210> SEQ ID NO 30
<211> LENGTH: 19
<212> TYPE: DNA
<213> ORGANISM: Artificial Sequence
<220> FEATURE:
<223> OTHER INFORMATION: synthetic oligo

<400> SEQUENCE: 30
tctgagtata agccgccca                                                  19

<210> SEQ ID NO 31
<211> LENGTH: 19
<212> TYPE: DNA
<213> ORGANISM: Artificial Sequence
<220> FEATURE:
<223> OTHER INFORMATION: synthetic oligo

<400> SEQUENCE: 31
atagaccgag cacagccaa                                                  19

<210> SEQ ID NO 32
<211> LENGTH: 21
```

```
<212> TYPE: DNA
<213> ORGANISM: Artificial Sequence
<220> FEATURE:
<223> OTHER INFORMATION: synthetic oligo

<400> SEQUENCE: 32
gaaccttctc aggattgagg t                                          21

<210> SEQ ID NO 33
<211> LENGTH: 21
<212> TYPE: DNA
<213> ORGANISM: Artificial Sequence
<220> FEATURE:
<223> OTHER INFORMATION: synthetic oligo

<400> SEQUENCE: 33
taacgaacga gactctggca t                                          21

<210> SEQ ID NO 34
<211> LENGTH: 22
<212> TYPE: DNA
<213> ORGANISM: Artificial Sequence
<220> FEATURE:
<223> OTHER INFORMATION: synthetic oligo

<400> SEQUENCE: 34
cggacatcta agggcatcac ag                                         22
```

ANC80 ENCODING SPHINGOLIPID-METABOLIZING PROTEINS FOR MITIGATING DISEASE-INDUCED TISSUE DAMAGE

CROSS-REFERENCE TO RELATED APPLICATIONS

This application is a U.S. continuation-in-part of PCT/US2019/021201 with an international filing date of Mar. 7, 2019, which claims priority to U.S. provisional application No. 62/692,185 filed Jun. 29, 2018; the contents of each are hereby incorporated by reference in their entirety into the present disclosure.

SEQUENCE LISTING

The instant application contains a Sequence Listing, created on Dec. 18, 2018; the file, in ASCII format, is designated 3710047A_SequenceListing_ST25.txt and is 39.9 kilobytes in size. The file is hereby incorporated by reference in its entirety into the instant application.

TECHNICAL FIELD

The present disclosure relates generally to the use of sphingolipid-metabolizing proteins to mitigate tissue damage resulting from disease. In pulmonary arterial hypertension, for example, exposure to sphingolipid metabolizing proteins such as acid ceramidase protein expressed from an Anc80 vector inhibits increases in pulmonary vascular resistance and elevation of mean pulmonary artery pressure that lead to pulmonary and cardiac damage and in some cases, cardiac failure.

BACKGROUND OF THE DISCLOSURE

Pulmonary arterial hypertension (PAH) is a devastating cardiopulmonary disease of the pre-capillary arterial system in the lungs. PAH is a specific type of pulmonary hypertension that is caused by the development of scar tissue in the tiny blood vessels of the lung. This scar tissue blocks the blood flow through the lungs and causes the pressure in those blood vessels to increase. Progressive remodeling of the pulmonary circulation leads to dramatic increases in pulmonary vascular resistance (PVR) and elevated mean pulmonary artery pressure. Normally, the right ventricle outputs blood with ease into low resistance lung anatomy. However, in PAH, this sustained increase in PVR working against normal outflow affects the right ventricle, which must contract with more force to overcome this level of resistance and eventually fails. In the extreme cases, PAH becomes deadly very quickly as right ventricular volume loading can increase greater than 5 times normal, distorting the function of the left ventricle. In this scenario, biventricular dysfunction is noted with rapid decline in cardiac output with death due to pump failure. There is also a high incidence of sudden death due to arrhythmias since stretching of the right ventricle/atria structures triggers deadly conditions.

In PAH, the pulmonary tissue is under a constant cycle of proliferation, clotting, fibrosis, and arterial remodeling. This cycle allows plexiform lesions to develop gradually in the pre-capillary arterial system. These lesions are areas of multiple closed vessel networks that become pathological and invade, destroy neighboring networks. The net effect is a progressive destruction of the majority of pulmonary microcirculation that increases PVR and leads to heart failure.

PAH is typically diagnosed in patients via catheterization and considered positive if mean pulmonary artery pressure (m PAP) is greater than 25 mmHg. Numerous drugs to lower pressure specific to the lung arterioles are given to address the symptom, however does not treat the vascular problem. The disease has 5 distinct groups by etiology, all causing elevation in mPAP: Group 1: Pediatric and or genetic form caused by BMPR2 mutations and others that cause smooth muscle proliferation. Group 2: Secondary to severe left heart failure; post capillary. Largest market since patients with ischemic heart disease often suffer from PAH. Group 3: Due to COPD and other lung disorders which lead to inflammation/debris triggers affecting circulation. Group 4: Thromboembolic: Acute cases from large clots in the pulmonary vasculature. Group 5: Idiopathic.

The standard of care for PAH is a well-developed array of drugs that reduce PVR in the pulmonary arterioles, by acting on 1 of 3 defined pathways: 1) nitric oxide (NO), 2) prostacyclin, and 3) endothelin I/II. The pathways reduce PVR by increasing nitric oxide to relax smooth muscle and dilate vessels, or by interfering with smooth muscle proliferation to prevent closure, directly help blood flow, and maintain patency. These pathways do not ameliorate or interrupt the formation of plexiform lesions. Plexiform lesions are prevalent in >80% of patients post mortem, whereby any drug therapy that was successful in lowering mean PAP for any period of time did not prevent right heart failure and subsequent death. In fact, all drugs are limited in PAH and just focus on pressure reduction, which is controversial. Thus, the use of drugs that alleviate mPAP and treat the cellular mechanisms is a challenge.

What is needed is a therapeutic method that provides long-term expression of a sphingolipid-metabolizing enzyme to inhibit cell death and senescence and initiate survival in cells and tissues damaged by disease such as PAH.

SUMMARY OF THE DISCLOSURE

A treatment for minimizing cellular/tissue damage resulting from disease, for example PAH, or injury (endothelial, vascular smooth muscle, and pneumocytes), which prevents further deterioration of the tissue, is currently unavailable. Gene therapy works by safely transferring an episomal (i.e. not integrated) DNA instruction for prolonged expression. This therapy, while it may not address the underlying cause of the disease itself, can help minimize the damage to tissues affected by the disease, for example, the poor pulmonary circulation resulting from PAH. Therefore, the present disclosure contemplates administration to the lungs via aerosol or nebulization of a synthetic, ancestral adenovirus, Anc80 that encodes a sphingolipid-metabolizing protein as a novel, robust treatment option for PAH.

The present disclosure therefore, provides a method for minimizing tissue damage resulting from PAH by administration of a sphingolipid metabolizing protein for promoting survival and restoring function of cells or tissue in vitro or in vivo. Administration is by means of a viral vector that encodes the sphingolipid-metabolizing protein; in one embodiment Anc80 that encodes expression of acid ceramidase is administered to a subject in need thereof for the treatment of PAH.

A sphingolipid-metabolizing protein is selected from the group consisting of (1) ceramidase; (2) sphingosine kinase (SPHK); (3) sphingosine-1-phosphate receptor (SIPR); (4) ceramidase kinase (CERK) or a combination of (1), (2), (3), and (4).

In one embodiment, the sphingolipid-metabolizing protein is a ceramidase. In one embodiment the sphingolipid-metabolizing protein is an acid ceramidase. In one embodiment, the sphingolipid-metabolizing protein is a neutral ceramidase. In yet another embodiment, the sphingolipid-metabolizing protein is an alkaline ceramidase. In one embodiment, ceramidase is encoded by a nucleic acid selected from the group consisting of SEQ ID NO: 1, SEQ ID NO: 6, SEQ ID NO: 7, SEQ ID NO: 8, SEQ ID NO: 9, SEQ ID NO: 10, SEQ ID NO: 11 and SEQ ID NO: 12.

In yet another aspect, the disclosure relates to a method in which the vector encoding the expression of sphingolipid-metabolizing protein is Anc80. In one embodiment, the nucleotide sequence of Anc80 that encodes the sphingolipid-metabolizing protein comprises the nucleotide sequence of SEQ ID NO: 20.

In another related aspect, the disclosure relates to a pharmaceutical composition comprising an Anc80 viral vector encoding a sphingolipid-metabolizing protein and a pharmaceutically acceptable carrier.

In yet another related aspect, the disclosure relates to an Anc80 viral vector encoding a sphingolipid-metabolizing protein for use in the treatment of PAH.

In one aspect, the disclosure relates to a method to improve patient outcome in patients with PAH comprising contacting lung cells or tissue with (1) an Anc80 that encodes ceramidase, (2) an ANC80 that encodes sphingosine kinase (SPHK), (3) an ANC80 that encodes sphingosine-1-phosphate receptor (S1PR) (4) an ANC80 that encodes a ceramide kinase (CERK), or any combination of (1), (2), (3) and (4).

Anc80 is a synthetic vector (see Zinn et al. In *Silico Reconstruction of the Viral Evolutionary Lineage Yields a Potent Gene Therapy Vector*, Cell Reports 12. 1056-1068 (2015), and U.S. Pat. No. 9,695,220; both references are hereby incorporated by reference), contains a nucleotide sequence that encodes acid ceramidase having the oligonucleotide sequence of SEQ ID NO: 1. In one embodiment, the Anc80 encoding AC has the oligonucleotide sequence of SEQ ID NO: 6. In another embodiment, the cells are contacted with Anc80 that encodes sphingosine kinase (SPHK) having the oligonucleotide sequence of SEQ ID NO: 2. In another embodiment, the sphingolipid metabolizing molecule is S1PR and the oligonucleotide encoding it has the sequence SEQ ID NO: 3. In another embodiment, the sphingolipid metabolizing molecule is CERK and the oligonucleotide encoding it has the sequence SEQ ID NO: 19)

In one aspect, the present disclosure relates to a method for treating a subject to mitigate or minimize the tissue damage that results from PAH or other disease or disorder, the method comprising administering to the subject a therapeutically effective dose of an Anc80 viral vector that codes for the expression of a sphingolipid-metabolizing protein. In one embodiment, the sphingolipid-metabolizing protein is selected from the group consisting of (1) a ceramidase; (2) sphingosine kinase (SPHK); (3) sphingosine-1-phosphate receptor (SIPR); (4) ceramidase kinase (CERK) or a combination of (1), (2), (3), and (4). Administration of the sphingolipid-metabolizing protein is via means know to those of skill in the art, for example atomizer or nebulizer.

Compositions comprising any combination of Anc80s that code for the expression of (1) a ceramidase, (2) sphingosine kinase (SPHK), (3) sphingosine-1-phosphate receptor (51PR) and a (4) CERK are encompassed by the present disclosure.

DETAILED DESCRIPTION OF THE DISCLOSURE

Figure 1:
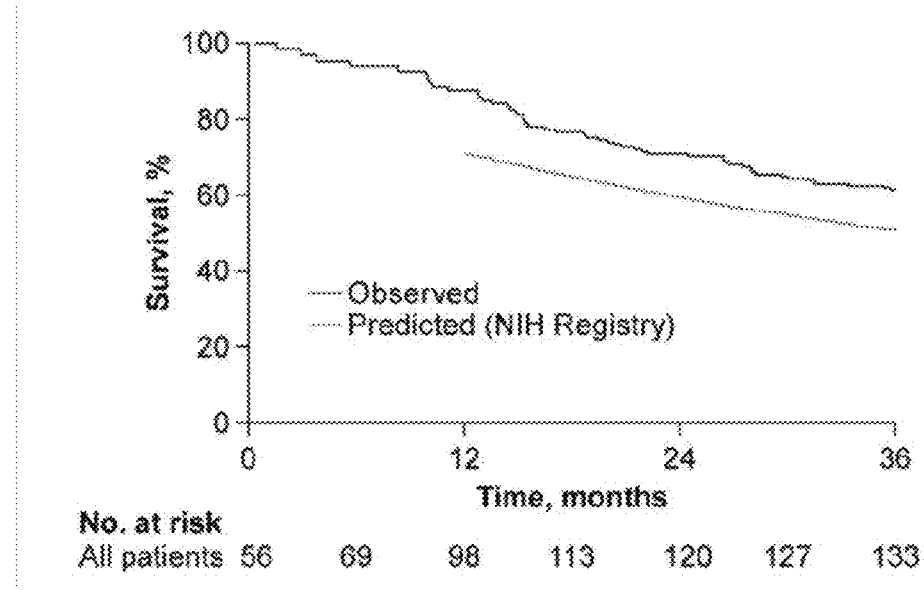
FIG. 1 is a graph showing percent survival for individuals with pulmonary arterial hypertension (PAH)

All patents, published applications and other references cited herein are hereby incorporated by reference into the present application.

In the description that follows, certain conventions will be followed as regards the usage of terminology. In general, terms used herein are intended to be interpreted consistently with the meaning of those terms, as they are known to those of skill in the art. Some definitions are provided purely for the convenience of the reader.

The term "cell or group of cells" is intended to encompass single cells as well as multiple cells either in suspension or in monolayers. Whole tissues also constitute a group of cells.

The term "ischemic" as it is known in the art refers to a deficiency in the supply of blood to a part of the body (such as the heart, brain or other organ/tissue) that is due to obstruction of the inflow of arterial blood as by the narrowing of arteries by spasm or disease.

The term "inhibit" or "inhibition" when used in conjunction with a discussion of senescence includes the ability of the sphingolipid-metabolizing proteins of the disclosure to reverse senescence, thereby returning to normal or near normal function.

The terms "stress", "stress-related events" or "cellular-stress" refers to a wide range of molecular changes that cells undergo in response to environmental stressors, such as extreme temperatures, exposure to toxins, mechanical damage, anoxia, and noise.

Pulmonary Arterial Hypertension

Pulmonary arterial hypertension (PAH) is one form of a broader condition known as pulmonary hypertension, which means high blood pressure in the lungs. In PAH, the rise in blood pressure is caused by changes in the cells that line the pulmonary arteries. These changes can cause the walls of the arteries to become stiff and thick, and extra tissue may form. The blood vessels may also become inflamed and tight. In many cases of pulmonary arterial hypertension, the cause is idiopathic (i.e., unknown). Other causes include heart abnormalities present at birth, HIV infection (Group I PAH); left-sided valvular heart disease such as mitral valve or aortic valve disease (Group 2 PAH); chronic obstructive pulmonary disease and other lung disease (Group 3 PAH); connective tissue/autoimmune disorders (such as scleroderma) and others.

PAH occurs when the very small arteries throughout the lungs narrow in diameter, which increases the resistance to blood flow through the lungs. Over time, the increased blood pressure can damage the heart. A number of diseases and conditions can cause PAH, and symptoms are similar to the symptoms often seen in more common diseases, such as asthma, chronic obstructive pulmonary disease (COPD), and heart failure.

Mitral Valve Prolapse

Mitral Valve Prolapse (MVP) is a common disorder afflicting at least 2% to 3% of the general population that affects ≈7.8 million individuals in the United States and >176 million people worldwide [Freed L A 1999, Devereux RB, 2001].

A canine model of a related disease, Myxomatous Mitral Valve Degeneration, MMVD, is used to further understanding of the role of Anc80 delivery of sphingolipid-metabolizing proteins in MVP.

The present technology is based on the use of sphingolipid metabolizing proteins in order to manipulate the fate of cells post stress-related events and during disease and aging. Different types of stress can initiate the signal transduction that leads to two major pathways: one can lead to cell death and the other leads to senescence, which is characterized by low cell function and arrested regeneration and amplification. In addition, senescent cells secrete different factors that can trigger an immune response and lead to inflammation and additional cell death. Cell senescence can be initiated not only by stress but also during aging. Both the cell death and cell senescence pathways involve sphingolipid metabolism mainly an increase in ceramide that can lead to both.

Ceramide has been shown to induce apoptotic cell death in different cells type including murine and human cardiomyocytes. On the other hand, sphingosine, one of the products of ceramide degradation can be phosphorylated to give rise to a major agent of cell survival and cardioprotection, sphingosine 1 phosphate.

There are also several studies that support association of the signaling lipid, ceramide, and its metabolizing enzymes with cellular and organismal aging and senescence. It has been reported that the intracellular level of ceramide increased during stress related signaling such as cell culture and aging.

Ceramidase, for example, acid ceramidase (AC) is required to hydrolyze ceramide into sphingosine and free fatty acids. Sphingosine is rapidly converted to sphingosine-1-phosphate (S1P), another important signaling lipid that counteracts the effects of ceramide and promotes cell survival. Thus, AC acts as a "rheostat" that regulates the levels of ceramide and S1P in cells, and as such participates in the complex and delicate balance between death and survival.

We have previously shown that AC expression is carefully regulated during oocyte maturation and early embryo development (Eliyahu, et al, 2010). We have also found that the complete "knock-out" of AC function in mice leads to embryo death between the 2 and 8-cell stage (Eliyahu, FASEB J, 2007). In addition, our previous publication (Eliyahu, FASEB J, 2010) showed that the ceramide-metabolizing enzyme, AC is expressed and active in human cumulus cells and follicular fluid, essential components of this environment, and that the levels of this enzyme are positively correlated with the quality of human embryos formed in vitro. These observations led to a new approach for oocyte and embryo culture that markedly improves the outcome of in vitro fertilization (IVF).

In this disclosure, we describe a strategy to reduce pulmonary arterial hypertension by increasing ceramide hydrolysis by overexpression of acid ceramidase. With this strategy, not only can we reduce ceramide levels but we also increase the reservoir of sphingosine which is the main building block for the pro-survival molecule sphingosine-1-phosphate (S1P).

Choice of Vehicle and Duration of Expression Needed

Methods and compositions for in vivo delivery of a construct that expresses a sphingolipid-metabolizing protein such as ceramidase were explored. For applications where more sustained expression of a sphingolipid metabolizing enzyme is required, expression from an Anc80 vector may be desirable.

Adeno-associated viruses have emerged as one of the most promising vectors in the field of gene therapy. Preclinical and clinical studies have validated the use of adeno-associated viral vectors (AAVs) as a safe and efficient delivery vehicle for gene transfer. AAV vectors are known to be expressed for several months or longer post administration; thus, they provide a more extensive time frame than modRNA.

More recently, Zinn et al. identified Anc80 as a highly potent in vivo gene therapy vector for targeting liver, muscle and retina. Anc80 virus, an in silico designed gene therapy vector, has demonstrated high gene expression levels in the liver, eye and ear compared to naturally occurring adeno-associated viral vectors (AAVs) that are currently in clinical development. Due to its synthetic nature, Anc80 does not circulate in humans, making it less likely to be recognized immunologically by antibodies against naturally-occurring AAVs. Anc80 also provides longer lasting expression. In addition, Anc80 expresses protein in much higher amounts than AAVs, so the amount of necessary virus is much less that leads to lower immune response.

The present disclosure, therefore, also provides a method for inhibiting or reducing pulmonary arterial hypertension by administration of a cocktail of Anc80 virus encoding sphingolipid metabolizing proteins. The treatment includes different combinations of Acid Ceramidase (AC) and/or Sphingosine Kinase (SPHK) and/or Sphingosine-1-phosphate receptor (S1PR) gene (cDNA). Anc80 virus, an in silico designed gene therapy vector, Anc80 has demonstrated high gene expression levels in the liver, eye and ear compared to naturally-occurring adeno-associated viral vectors (AAVs) that are currently in clinical development. Anc80, an engineered gene therapy vector, is synthetic in nature and has been shown to reduce cross-reactivity with commonly used AAV vectors. Anc80 is a potent gene therapy vector that is not known to circulate in humans, making it less likely to cross-react immunologically with naturally occurring AAVs.

Sphinqolipid-Metabolizing Proteins

In one embodiment, a composition useful for practicing the method of the present disclosure may include either individually or in different combinations Anc80 vectors encoding the following sphingolipid-metabolizing proteins: ceramidase (acid, neutral or alkaline), sphingosine kinase (SPHK), sphingosine-1-phosphate receptor (S1PR), and a ceramide kinase (CERK). In one embodiment, the sphingolipid-metabolizing protein is a ceramidase.

Ceramidase is an enzyme that cleaves fatty acids from ceramide, producing sphingosine (SPH), which in turn is phosphorylated by a sphingosine kinase to form sphingosine-1-phosphate (S1P). Ceramidase is the only enzyme that can regulate ceramide hydrolysis to prevent cell death and SHPK is the only enzyme that can synthesize sphingosine 1 phosphate (S1P) from sphingosine (the ceramide hydrolysis product) to initiate cell survival. S1PR, a G protein-coupled receptor binds the lipid-signaling molecule S1P to induce cell proliferation, survival, and transcriptional activation. CERK is an phosphatase that phosphorylates ceramide into ceramide 1 phosphate to induce cell survival.

Presently, 7 human ceramidases encoded by 7 distinct genes have been cloned:
  acid ceramidase (ASAH1)—associated with cell survival;
  neutral ceramidase (ASAH2, ASAH2B, ASAH2C)—protective against inflammatory cytokines;
  alkaline ceramidase 1 (ACER1)—mediating cell differentiation by controlling the generation of SPH and S1P;
  alkaline ceramidase 2 (ACER2)—important for cell proliferation and survival; and
  alkaline ceramidase 3 (ACER3).

The nucleotide sequences for nucleic acids encoding these ceramidases are shown in Table 1.

In one embodiment, Anc80, a relatively nascent technology, has shown considerable potential as a delivery vehicle for gene therapy in disease, for example, cardiac disease, hearing loss, vision loss and neurodegenerative diseases. Anc80 as an engineered gene therapy vector is synthetic in nature and is not known to circulate in humans. It has been shown to have reduced cross-reactivity with commonly used AAV vectors. Anc80 therefore is a potent gene therapy vector, which is less likely to be recognized immunologically by antibodies against naturally occurring AAVs.

Advantages

An Anc80 vector encoding acid ceramidase (Anc80.AC) has multiple advantages over other potential anti-apoptotic factors.

Low Toxicity

Low or no toxicity: The AC protein, by itself, is not toxic. Physiological enzymes are not expected to have toxic effects. The biological function of AC is the control of ceramide metabolism has no direct influence other cellular signaling. Treated cells present only a modest increase in AC generation in cells post gene therapy treatment. The AC protein level expressed after treatment is far below extraordinarily high levels reported in aberrant diseased cells with poorly understood mechanisms. The AC protein exists in two forms, and undergoes a transformation from an inactive to active form in the cell. The inactive AC precursor undergoes an auto-self cleavage to the active enzyme, which is responsible for hydrolyzing ceramide to sphingosine. This exquisitely evolved self-regulating mechanism, call the Sphingolipid Rheostat, regulates, by hydrolysis toxic levels of ceramides in the cell after exposure to stress. The transfection of cells with Anc80.AC can increase the cellular reservoir of inactive precursor, thereby allowing physiological sphingolipid levels to regulate the conversion to the active AC enzyme necessary for cellular robustness and organism survival. In addition, Eliyahu lab created mouse model that is constantly overexpressing the AC enzyme (COEAC) in all tissues. The COEAC mice viability provides evidence that AC is a non-toxic protein.

Ease of Delivery

As mentioned, Anc80, an engineered gene therapy vector, is synthetic in nature and shown to reduce cross-reactivity with commonly used AAV vectors. Anc80 is a potent gene therapy vector that is not known to circulate in humans, making it less likely to be recognized immunologically by antibodies against naturally occurring AAVs. Recently, it has been shown successful, robust, transfection of Anc80 virus into liver, eye and ear tissue in vivo (see Magali Trayssac, Yusuf A. Hannun, and Lina M. Obeid. Role of sphingolipids in senescence: implication in aging and age-related diseases. J. Clin. Inves. 2018; 128(7):2702-2712, which is hereby incorporated by reference.)

In one embodiment, Anc80.AC is administered to at-risk tissue by aerosolization of a composition comprising an Anc80 viral vector that codes for the expression of acid ceramidase. Methods of administration also include intratracheal injection Unique Physiological Function of Acid Ceramidase Increase in ceramide level can have different outcomes leading to cell death and/or senescence. Ceramidase is the only enzyme that can hydrolyze ceramide and therefore, the only enzyme that can directly decrease the levels of ceramide in cells.

Table 1 contains the nucleotide sequences to be encoded by the vectors disclosed for use in practicing the method.

TABLE 1

| Gene | Open Reading Frame |
|---|---|
| ASAH1 transcript variant 1 (ACv1) | ATGCCGGGCCGGAGTTGCGTCGCCTTAGTCCTCCTGGCTGCCGCCGTCAGCTGTGCCGTCGCGCA<br>GCACGCGCCGCCGTGGACAGAGGACTGCAGAAAATCAACCTATCCTCCTTCAGGACCAACGTAC<br>AGAGGTGCAGTTCCATGGTACACCATAAATCTTGACTTACCACCCTACAAAAGATGGCATGAATT<br>GATGCTTGACAAGGCACCAGTGCTAAAGGTTATAGTGAATTCTCTGAAGAATATGATAAATACAT<br>TCGTGCCAAGTGGAAAAATTATGCAGGTGGTGGATGAAAAATTGCCTGGCCTACTTGGCAACTTT<br>CCTGGCCCTTTTGAAGAGGAAATGAAGGGTATTGCCGCTGTTACTGATATACCTTTAGGAGAGAT<br>TATTTCATTCAATATTTTTTATGAATTATTTACCATTTGTACTTCAATAGTAGCAGAAGACAAAAAA<br>GGTCATCTAATACATGGGAGAAACATGGATTTTGGAGTATTTCTTGGGTGGAACATAAATAATGA<br>TACCTGGGTCATAACTGAGCAACTAAAACCTTTAACAGTGAATTTGGATTTCCAAAGAAACAACA<br>AAACTGTCTTCAAGGCTTCAAGCTTTGCTGGCTATGTGGGCATGTTAACAGGATTCAAACCAGGA<br>CTGTTCAGTCTTACACTGAATGAACGTTTCAGTATAAATGGTGGTTATCTGGGTATTCTAGAATGG<br>ATTCTGGGAAAGAAAGATGTCATGTGGATAGGGTTCCTCACTAGAACAGTTCTGGAAAATAGCA<br>CAAGTTATGAAGAAGCCAAGAATTTATTGACCAAGACCAAGATATTGGCCCCAGCCTACTTTATC<br>CTGGGAGGCAACCAGTCTGGGGAAGGTTGTGTGATTACACGAGACAGAAAGGAATCATTGGAT<br>GTATATGAACTCGATGCTAAGCAGGGTAGATGGTATGTGGTACAAACAAATTATGACCGTTGGA<br>AACATCCCTTCTTCCTTGATGATCGCAGAACGCCTGCAAAGATGTGTCTGAACCGCACCAGCCAA<br>GAGAATATCTCATTTGAAACCATGTATGATGTCCTGTCAACAAAACCTGTCCTCAACAAGCTGACC<br>GTATACACAACCTTGATAGATGTTACCAAAGGTCAATTCGAAACTTACCTGCGGGACTGCCCTGA<br>CCCTTGTATAGGTTGGTGA (SEQ ID NO: 1) |
| Sphk1 | ATGGATCCAGTGGTCGGTTGCGGACGTGGCCTCTTTGGTTTTGTTTTCTCAGCGGGCGGCCCCCG<br>GGGCGTGCTCCCGCGGCCCTGCCGCGTGCTGGTGCTGCTGAACCCGCGCGGCGGCAAGGGCAA<br>GGCCTTGCAGCTCTTCCGGAGTCACGTGCAGCCCCTTTTGGCTGAGGCTGAAATCTCCTTCACGCT<br>GATGCTCACTGAGCGGCGGAACCACGCGCGGGAGCTGGTGCGGTCGGAGGAGCTGGGCCGCTG<br>GGACGCTCTGGTGGTCATGTCTGGAGACGGGCTGATGCACGAGGTGGTGAACGGGCTCATGGA<br>GCGGCCTGACTGGGAGACCGCCATCCAGAAGCCCCTGTGTAGCCTCCCAGCAGGCTCTGGCAAC<br>GCGCTGGCAGCTTCCTTGAACCATTATGCTGGCTATGAGCAGGTCACCAATGAAGACCTCCTGAC<br>CAACTGCACGCTATTGCTGTGCCGCCGGCTGCTGTCACCCATGAACCTGCTGTCTCTGCACACGGC<br>TTCGGGGCTGCGCCTCTTCTCTGTGCTCAGCCTGGCCTGGGGCTTCATTGCTGATGTGGACCTAG<br>AGAGTGAGAAGTATCGGCGTCTGGGGGAGATGCGCTTCACTCTGGGCACCTTCCTGCGTCTGGC<br>AGCCCTGCGCACCTACCGCGGCCGACTGGCCTACCTCCCTGTAGGAAGAGTGGGTTCCAAGACAC<br>CTGCCTCCCCCGTTGTGGTCCAGCAGGGCCCGGTAGATGCACACCTTGTGCCACTGGAGGAGCCA<br>GTGCCCTCTCACTGGACAGTGGTGCCCGACGAGGACTTTGTGCTAGTCCTGGCACTGCTGCACTC<br>GCACCTGGGCAGTGAGATGTTTGCTGCACCCATGGGCCGCTGTGCAGCTGGCGTCATGCATCTGT<br>TCTACGTGCGGGCGGGAGTGTCTCGTGCCATGCTGCTGCGCCTCTTCCTGGCCATGGAGAAGGG<br>CAGGCATATGGAGTATGAATGCCCCTACTTGGTATATGTGCCCGTGGTCGCCTTCCGCTTGGAGC<br>CCAAGGATGGGAAAGGTGTGTTTGCAGTGGATGGGGAATTGATGGTTAGCGAGGCCGTGCAGG<br>GCCAGGTGCACCCAAACTACTTCTGGATGGTCAGCGGTTGCGTGGAGCCCCCGCCCAGCTGGAA<br>GCCCCAGCAGATGCCACCGCCAGAAGAGCCCTTATGA (SEQ ID NO: 2) |
| S1PR2 | ATGGGCAGCTTGTACTCGGAGTACCTGAACCCCAACAAGGTCCAGGAACACTATAATTATACCAA<br>GGAGACGCTGGAAACGCAGGAGACGACCTCCCGCCAGGTGGCCTCGGCCTTCATCGTCATCCTCT<br>GTTGCGCCATTGTGGTGGAAAACCTTCTGGTGCTCATTGCGGTGGCCCGAAACAGCAAGTTCCAC<br>TCGGCAATGTACCTGTTTCTGGGCAACCTGGCCGCCTCCGATCTACTGGCAGGCGTGGCCTTCGT<br>AGCCAATACCTTGCTCTCTGGCTCTGTCACGCTGAGGCTGACGCCTGTGCAGTGGTTTGCCCGGG<br>AGGGCTCTGCCTTCATCACGCTCTCGGCCTCTGTCTTCAGCCTCCTGGCCATCGCCATTGAGCGCC<br>ACGTGGCCATTGCCAAGGTCAAGCTGTATGGCAGCGACAAGAGCTGCCGCATGCTTCTGCTCATC<br>GGGGCCTCGTGGCTCATCTCGCTGGTCCTCGGTGGCCTGCCCATCCTTGGCTGGAACTGCCTGGG |

TABLE 1-continued

| Gene | Open Reading Frame |
|---|---|
| | CCACCTCGAGGCCTGCTCCACTGTCCTGCCTCTCTACGCCAAGCATTATGTGCTGTGCGTGGTGAC<br>CATCTTCTCCATCATCCTGTTGGCCATCGTGGCCCTGTACGTGCAGCATCTACTGCGTGGTCCGCTC<br>AAGCCACGCTGACATGGCCGCCCCGCAGACGCTAGCCCTGCTCAAGACGGTCACCATCGTGCTAG<br>GCGTCTTTATCGTCTGCTGGCTGCCCGCCTTCAGCATCCTCCTTCTGGACTATGCCTGTCCCGTCCA<br>CTCCTGCCCGATCCTCTACAAAGCCCACTACTTTTTCGCCGTCTCCACCCTGAATTCCCTGCTCAAC<br>CCCGTCATCTACACGTGGCGCAGCCGGGACCTGCGGCGGGAGGTGCTTCGGCCGCTGCAGTGCT<br>GGAGGCCGGGGGTGGGGGTGCAAGGACGGAGGCGGGGCGGGACCCCGGGCCACCACCTCCTG<br>CCACTCCGCAGCTCCAGCTCCCTGGAGAGGGGCATGCACATGCCCACGTCACCCACGTTTCTGGA<br>GGGCAACACGGTGGTCATG (SEQ ID NO: 3) |
| Firefly<br>luciferase | ATGGCCGATGCTAAGAACATTAAGAAGGGCCCTGCTCCCTTCTACCCTCTGGAGGATGGCACCGC<br>TGGCGAGCAGCTGCACAAGGCCATGAAGAGGTATGCCCTGGTGCCTGGCACCATTGCCTTCACC<br>GATGCCCACATTGAGGTGGACATCACCTATGCCGAGTACTTCGAGATGTCTGTGCGCCTGGCCGA<br>GGCCATGAAGAGGTACGGCCTGAACACCAACCACCGCATCGTGGTGTGCTCTGAGAACTCTCTGC<br>AGTTCTTCATGCCAGTGCTGGGCGCCCTGTTCATCGGAGTGGCCGTGGCCCCTGCTAACGACATT<br>TACAACGAGCGCGAGCTGCTGAACAGCATGGGCATTTCTCAGCCTACCGTGGTGTTCGTGTCTAA<br>GAAGGGCCTGCAGAAGATCCTGAACGTGCAGAAGAAGCTGCCTATCATCCAGAAGATCATCATC<br>ATGGACTCTAAGACCGACTACCAGGGCTTCCAGAGCATGTACACATTCGTGACATCTCATCTGCCT<br>CCTGGCTTCAACGAGTACGACTTCGTGCCAGAGTCTTTCGACAGGGACAAAACCATTGCCCTGAT<br>CATGAACAGCTCTGGGTCTACCGGCCTGCCTAAGGGCGTGGCCCTGCCTCATCGCACCGCCTGTG<br>TGCGCTTCTCTCACGCCCGCGACCCTATTTTCGGCAACCAGATCATCCCCGACACCGCTATTCTGA<br>GCGTGGTGCCATTCCACCACGGCTTCGGCATGTTCACCACCCTGGGCTACCTGATTTGCGGCTTTC<br>GGGTGGTGCTGATGTACCGCTTCGAGGAGGAGCTGTTCCTGCGCAGCCTGCAAGACTACAAAAT<br>TCAGTCTGCCCTGCTGGTGCCAACCCTGTTCAGCTTCTTCGCTAAGAGCACCCTGATCGACAAGTA<br>CGACCTGTCTAACCTGCACGAGATTGCCTCTGGCGGCGCCCCACTGTCTAAGGAGGTGGGCGAA<br>GCCGTGGCCAAGCGCTTTCATCTGCCAGGCATCCGCCAGGGCTACGGCCTGACCGAGACAACCA<br>GCGCCATTCTGATTACCCCAGAGGGCGACGACAAGCCTGGCGCCGTGGGCAAGGTGGTGCCATT<br>CTTCGAGGCCAAGGTGGTGGACCTGGACACCGGCAAGACCCTGGGAGTGAACCAGCGCGGCGA<br>GCTGTGTGTGCGCGGCCCTATGATTATGTCCGGCTACGTGAATAACCCTGAGGCCACAAACGCCC<br>TGATCGACAAGGACGGCTGGCTGCACTCTGGCGACATTGCCTACTGGGACGAGGACGAGCACTT<br>CTTCATCGTGGACCGCCTGAAGTCTCTGATCAAGTACAAGGGCTACCAGGTGGCCCCAGCCGAGC<br>TGGAGTCTATCCTGCTGCAGCACCCTAACATTTTCGACGCCGGAGTGGCCGGCCTGCCCGACGAC<br>GATGCCGGCGAGCTGCCTGCCGCCGTCGTCGTGCTGGAACACGGCAAGACCATGACCGAGAAG<br>GAGATCGTGGACTATGTGGCCAGCCAGGTGACAACCGCCAAGAAGCTGCGCGGCGGAGTGGTG<br>TTCGTGGACGAGGTGCCCAAGGGCCTGACCGGCAAGCTGGACGCCCGCAAGATCCGCGAGATCC<br>TGATCAAGGCTAAGAAGGCGGCAAGATCGCCGTGTAA (SEQ ID NO: 4) |
| nGFP | ATGGTGAGCAAGGGCGAGGAGCTGTTCACCGGGGTGGTGCCCATCCTGGTCGAGCTGGACGGC<br>GACGTAAACGGCCACAAGTTCAGCGTGTCCGGCGAGGGCGAGGGCGATGCCACCTACGGCAAG<br>CTGACCCTGAAGTTCATCTGCACCACCGGCAAGCTGCCCGTCCCCTGGCCCACCCTCGTGACCACC<br>CTGACCTACGGCGTGCAGTGCTTCAGCCGCTACCCCGACCACATGAAGCAGCACGACTTCTTCAA<br>GTCCGCCATGCCCGAAGGCTACGTCCAGGAGCGCACCATCTTCTTCAAGGACGACGGCAACTACA<br>AGACCCGCGCCGAGGTGAAGTTCGAGGGCGACACCCTGGTGAACCGCATCGAGCTGAAGGGCA<br>TCGACTTCAAGGAGGACGGCAACATCCTGGGGCACAAGCTGGAGTACAACTACAACAGCCACAA<br>CGTCTATATCATGGCCGACAAGCAGAAGAACGGCATCAAGGTGAACTTCAAGATCCGCCACAAC<br>ATCGAGGACGGCAGCGTGCAGCTCGCCGACCACTACCAGCAGAACACCCCCATCGGCGACGGCC<br>CCGTGCTGCTGCCCGACAACCACTACCTGAGCACCCAGTCCGCCCTGAGCAAAGACCCCAACGAG<br>AAGCGCGATCACATGGTCCTGCTGGAGTTCGTGACCGCCGCCGGGATCACTCTCGGCATGGACG<br>AGCTGTACAAGGGAGATCAAAAAAGAAGAGAAAGGTAGGCGATCAAAAAAGAAGAGAAAG<br>GTAGGTGATCCAAAAAAGAAGAGAAAGGTATAA (SEQ ID NO: 5) |
| ASAH1<br>transcript<br>variant 2<br>(ACv2) | ATGAACTGCTGCATCGGGCTGGGAGAGAAAGCTCGCGGGTCCCACCGGGCCTCCTACCCAAGTC<br>TCAGCGCGCTTTTCACCGAGGCCTCAATTCTGGGATTTGGCAGCTTTGCTGTGAAAGCCCAATGG<br>ACAGAGGACTGCAGAAAATCAACCTATCCTCCTTCAGGACCAACGTACAGAGGTGCAGTTCCATG<br>GTACACCATAAATCTTGACTTACCACCCTACAAAGATGGCATGAATTGATGCTTGACAAGGCAC<br>CAGTGCTAAAGGTTATAGTGAATTCTCTGAAGAAATATGATAAATACATTCGTGCCAAGTGGAAAA<br>ATTATGCAGGTGGTGGATGAAAAATTGCCTGGCCTACTTGGCAACTTTCCTGGCCCTTTTGAAGA<br>GGAAATGAAGGGTATTGCCGCTGTTACTGATATACCTTTAGGAGAGATTATTTCATTCAATATTTT<br>TTATGAATTATTTACCATTTGTACTTCAATAGTAGCAGAAGACAAAAAAGGTCATCTAATACATGG<br>GAGAAACATGGATTTTGGAGTATTTCTTGGGTGGAACATAAATAATGATAACCTGGGTCATAACTG<br>AGCAACTAAAACCTTTAACAGTGAATTTGGATTTCCAAAGAAACAAACAAAACTGTCTTCAAGGCTT<br>CAAGCTTTGCTGGCTATGTGGGCATGTTAACAGGATTCAAACCAGGACTGTTCAGTCTTACACTG<br>AATGAACGTTTCAGTATAAATGGTGGTTATCTGGGTATTCTAGAATGGATTCTGGGAAAGAAGA<br>TGTCATGTGGATAGGGTTCCTCACTAGAACAGTTCTGGAAAATAGCACAAGTTATGAAGAAGCCA<br>AGAATTTATTGACCAAGCACAAGATATTGGCCCCAGCCTACTTATCCTGGGAGGCAACCAGTCT<br>GGGGAAGGTTGTGTGATTACACGAGACAGAAAGGAATCATTGGATGTATATGAACTCGATGCTA<br>AGCAGGGTAGATGGTATGTGGTACAAACAAATTATGACCGTTGGAAACATCCCTTCTTCCTTGAT<br>GATCGCAGAACGCCTGCAAAGATGTGTCTGAACCGCACCAGCCAAGAGAATATCTCATTTGAAAC<br>CATGTATGATGTCCTGTCAACAAAACCTGTCCTCAACAAGCTGACCGTATACACAACCTTGATAGA<br>TGTTACCAAAGGTCAATTCGAAACTTACCTGCGGGACTGCCCTGACCCTTGTATAGGTTGGTGA<br>(SEQ ID NO: 6) |
| ASAH1<br>transcript<br>variant 3 | ATGAACTGCTGCATCGGGCTGGGAGAGAAAGCTCGCGGGTCCCACCGGGCCTCCTACCCAAGTC<br>TCAGCGCGCTTTTCACCGAGGCCTCAATTCTGGGATTTGGCAGCTTTGCTGTGAAAGCCCAATGG<br>ACAGAGGACTGCAGAAAATCAACCTATCCTCCTTCAGGACCAACTGTCTTCCTGCTGTTATAAGG<br>TACAGAGGTGCAGTTCCATGGTACACCATAAATCTTGACTTACCACCCTACAAAGATGGCATGA<br>ATTGATGCTTGACAAGGCACCAGTGCCTGGCCTACTTGGCAACTTTCCTGGCCCTTTTGAAGAGG<br>AAATGAAGGGTATTGCCGCTGTTACTGATATACCTTTAGGAGAGATTATTTCATTCAATATTTTT |

TABLE 1-continued

| Gene | Open Reading Frame |
|---|---|
| | ATGAATTATTTACCATTTGTACTTCAATAGTAGCAGAAGACAAAAAAGGTCATCTAATACATGGG<br>AGAAACATGGATTTTGGAGTATTTCTTGGGTGGAACATAAATAATGATACCTGGGTCATAACTGA<br>GCAACTAAAACCTTTAACAGTGAATTTGGATTTCCAAAGAAACAACAAAACTGTCTTCAAGGCTTC<br>AAGCTTTGCTGGCTATGTGGGCATGTTAACAGGATTCAAACCAGGACTGTTCAGTCTTACACTGA<br>ATGAACGTTTCAGTATAAATGGTGGTTATCTGGGTATTCTAGAATGGATTCTGGGAAAGAAAGAT<br>GTCATGTGGATAGGGTTCCTCACTAGAACAGTTCTGGAAAATAGCACAAGTTATGAAGAAGCCA<br>AGAATTTATTGACCAAGACCAAGATATTGGCCCCAGCCTACTTTATCCTGGGAGGCAACCAGTCT<br>GGGGAAGGTTGTGTGATTACACGAGACAGAAAGGAATCATTGGATGTATATGAACTCGATGCTA<br>AGCAGGGTAGATGGTATGTGGTACAAACAAATTATGACCGTTGGAAACATCCCTTCTTCCTTGAT<br>GATCGCAGAACGCCTGCAAAGATGTGTCTGAACCGCACCAGCCAAGAGAATATCTCATTTGAAAC<br>CATGTATGATGTCCTGTCAACAAAACCTGTCCTCAACAAGCTGACCGTATACACAACCTTGATAGA<br>TGTTACCAAAGGTCAATTCGAAACTTACCTGCGGGACTGCCCTGACCCTTGTATAGGTTGGTGA<br>(SEQ ID NO: 7) |
| ASAH2<br>transcript<br>variant 1 | ATGGCCAAACGCACCTTCTCTAACTTGGAGACATTCCTGATTTTCCTCCTTGTAATGATGAGTGCC<br>ATCACAGTGGCCCTTCTCAGCCTCTTGTTTATCACCAGTGGGACCATTGAAAACCACAAAGATTTA<br>GGAGGCCATTTTTTTTCAACCACCCAAAGCCCTCCAGCCACCCAGGGCTCCACAGCTGCCCAACGC<br>TCCACAGCCACCCAGCATTCCACAGCCACCCAGAGCTCCACAGCCACTCAAACTTCTCCAGTGCCT<br>TTAACCCCAGAGTCTCCTCTATTTCAGAACTTCAGTGGCTACCATATTGGTGTTGGACGAGCTGAC<br>TGCACAGGACAAGTAGCAGATATCAATTTGATGGGCTATGGCAAATCCGGCCAGAATGCACAGG<br>GCATCCTCACCAGGCTATACAGTCGTGCCTTCATCATGGCAGAACCTGATGGGTCCAATCGAACA<br>GTGTTTGTCAGCATCGACATAGGCATGGTATCACAAAGGCTCAGGCTGGAGGTCCTGAACAGAC<br>TGCAGAGTAAATATGGCTCCCTGTACAGAAGAGATAATGTCATCCTGAGTGGCACTCACACTCAT<br>TCAGGTCCTGCAGGATATTTCCAGTATACCGTGTTTGTAATTGCCAGTGAAGGATTTAGCAATCAA<br>ACTTTTCAGCACATGGTCACTGGTATCTTGAAGAGCATTGACATAGCACACACAAATATGAAACC<br>AGGCAAAATCTTCATCAATAAAGGAAATGTGGATGGTGTGCAGATCAACAGAAGTCCGTATTCTT<br>ACCTTCAAAATCCGCAGTCAGAGAGAGCAAGGTATTCTTCAAATACAACAAGGAAATGATAGTT<br>TTGAAAATGGTAGATTTGAATGGAGATGACTTGGGCCTTATCAGCTGGTTTGCCATCCACCCGGT<br>CAGCATGAACAACAGTAACCATCTTGTAAACAGTGACAATGTGGGCTATGCATCTTACCTGCTTG<br>AGCAAGAGAAGAACAAAGGATATCTACCTGGACAGGGGCCATTTGTAGCAGCCTTTGCTTCATCA<br>AACCTAGGAGATGTGTCCCCCAACATTCTTGGACCACGTTGCATCAACACAGGAGAGTCCTGTGA<br>TAACGCCAATAGCACTTGTCCCATTGGTGGGCCTAGCATGTGCATTGCTAAGGGACCTGGACAGG<br>ATATGTTTGACAGCACACAAATTATAGGACGGGCATGTATCAGAGAGCAAAGGAACTCTATGCC<br>TCTGCCTCCCAGGAGGTAACAGGACCACTGGCTTCAGCACACCAGTGGGTGGATATGACAGATG<br>TGACTGTCTGGCTCAATTCCACACATGCATCAAAAACATGTAAACCAGCATTGGGCTACAGTTTTG<br>CAGCTGGCACTATTGATGGAGTTGGAGGCCTCAATTTTACACAGGGGAAAACAGAAGGGGATCC<br>ATTTTTGGGACACCATTCGGGACCAGATCCTGGGAAAGCCATCTGAAGAAATTAAAGAATGTCATA<br>AACCAAAGCCCATCCTTCTTCACACCGGAGAACTATCAAAACCTCACCCCTGGCATCCAGACATTG<br>TTGATGTTCAGATTATTACCCTTGGGTCCTTGGCCATAACTGCCATCCCCGGGGAGTTTACGACCA<br>TGTCTGGACGAAGACTTCGAGAGGCAGTTCAAGCAGAATTTGCATCTCATGGGATGCAGAACAT<br>GACTGTTGTTATTTCAGGTCTATGCAACGTCTATACACATTACATTACCACTTATGAAGAATACCA<br>GGCTCAGCGATATGAGGCAGCATCGACAATTTATGGACCGCACACATTATCTGCTTACATTCAGC<br>TCTTCAGAAACCTTGCTAAGGCTATTGCTACGGACACGGTAGCCAACCTGAGCAGAGGTCCAGAA<br>CCTCCCTTTTTCAAACAATTAATAGTTCCATTAATTCCTAGTATTGTGGATAGAGCACCAAAAGGC<br>AGAACTTTCGGGGATGTCCTGCAGCCAGCAAAAACCTGAATACAGAGTGGGGGAAGTTGCTGAAG<br>TTATATTTGTAGGTGCTAACCCCGAAGAATTCAGTACAAAACCAGACCCATCAGACCTTCCTCACTG<br>TGGAGAAATATGAGGCTACTTCAACATCGTGGCAGATAGTGTGTAATGATGCCTCCTGGGAGACT<br>CGTTTTTATTGGCACAAGGGACTCCTGGGTCTGAGTAATGCAACAGTGGAATGGCATATTCCAGA<br>CACTGCCCAGCCTGGAATCTACAGAATAAGATATTTTGGACACAATCGGAAGCAGGACATTCTGA<br>AGCCTGCTGTCATACTTTCATTTGAAGGCACTTCCCCGGCTTTTGAAGTTGTAACTATTTAGTGA<br>(SEQ ID NO: 8) |
| ASAH2<br>transcript<br>variant 2 | ATGGCCAAACGCACCTTCTCTAACTTGGAGACATTCCTGATTTTCCTCCTTGTAATGATGAGTGCC<br>ATCACAGTGGCCCTTCTCAGCCTCTTGTTTATCACCAGTGGGACCATTGAAAACCACAAAGATTTA<br>GGAGGCCATTTTTTTTCAACCACCCAAAGCCCTCCAGCCACCCAGGGCTCCACAGCTGCCCAACGC<br>TCCACAGCCACCCAGCATTCCACAGCCACCCAGAGCTCCACAGCCACTCAAACTTCTCCAGTGCCT<br>TTAACCCCAGAGTCTCCTCTATTTCAGAACTTCAGTGGCTACCATATTGGTGTTGGACGAGCTGAC<br>TGCACAGGACAAGTAGCAGATATCAATTTGATGGGCTATGGCAAATCCGGCCAGAATGCACAGG<br>GCATCCTCACCAGGCTATACAGTCGTGCCTTCATCATGGCAGAACCTGATGGGTCCAATCGAACA<br>GTGTTTGTCAGCATCGACATAGGCATGGTATCACAAAGGCTCAGGCTGGAGGTCCTGAACAGAC<br>TGCAGAGTAAATATGGCTCCCTGTACAGAAGAGATAATGTCATCCTGAGTGGCACTCACACTCAT<br>TCAGGTCCTGCAGGATATTTCCAGTATACCGTGTTTGTAATTGCCAGTGAAGGATTTAGCAATCAA<br>ACTTTTCAGCACATGGTCACTGGTATCTTGAAGAGCATTGACATAGCACACACAAATATGAAACC<br>AGGCAAAATCTTCATCAATAAAGGAAATGTGGATGGTGTGCAGATCAACAGAAGTCCGTATTCTT<br>ACCTTCAAAATCCGCAGTCAGAGAGAGCAAGGTATTCTTCAAATACAACAAGGAAATGATAGTT<br>TTGAAAATGGTAGATTTGAATGGAGATGACTTGGGCCTTATCAGCTGGTTTGCCATCCACCCGGT<br>CAGCATGAACAACAGTAACCATCTTGTAAACAGTGACAATGTGGGCTATGCATCTTACCTGCTTG<br>AGCAAGAGAAGAACAAAGGATATCTACCTGGACAGGGGCCATTTGTAGCAGCCTTTGCTTCATCA<br>AACCTAGGAGATGTGTCCCCCAACATTCTTGGACCACGTTGCATCAACACAGGAGAGTCCTGTGA<br>TAACGCCAATAGCACTTGTCCCATTGGTGGGCCTAGCATGTGCATTGCTAAGGGACCTGGACAGG<br>ATATGTTTGACAGCACACAAATTATAGGACGGGCATGTATCAGAGAGCAAAGTCAAAACATGT<br>AAACCAGCATTGGGCTACAGTTTTGCAGCTGGCACTATTGATGGAGTTGGAGGCCTCAATTTTAC<br>ACAGGGGAAAACAGAAGGGGATCCATTTTTGGGACACCATTCGGGACCAGATCCTGGGAAAGCC<br>ATCTGAAGAAATTAAAGAATGTCATAAACCAAAGCCCATCCTTCTTCACACCGGAGAACTATCAA<br>AACCTCACCCCTGGCATCCAGACATTGTTGATGTTCAGATTATTACCCTTGGGTCCTTGGCCATAA<br>CTGCCATCCCCGGGGAGTTTACGACCATGTCTGGACGAAGACTTCGAGAGGCAGTTCAAGCAGA<br>ATTTGCATCTCATGGGATGCAGAACATGACTGTTGTTATTTCAGGTCTATGCAACGTCTATACACA<br>TTACATTACCACTTATGAAGAATACCAGGCTCAGCGATATGAGGCAGCATCGACAATTTATGGAC |

TABLE 1-continued

| Gene | Open Reading Frame |
|---|---|
| | CGCACACATTATCTGCTTACATTCAGCTCTTCAGAAACCTTGCTAAGGCTATTGCTACGGACACGG<br>TAGCCAACCTGAGCAGAGGTCCAGAACCTCCCTTTTTCAAACAATTAATAGTTCCATTAATTCCTA<br>GTATTGTGGATAGAGCACCAAAAGGCAGAACTTTCGGGGATGTCCTGCAGCCAGCAAAACCTGA<br>ATACAGAGTGGGGGAAGTTGCTGAAGTTATATTTGTAGGTGCTAACCCGAAGAATTCAGTACAA<br>AACCAGACCCATCAGACCTTCCTCACTGTGGAGAAATATGAGGCTACTTCAACATCGTGGCAGAT<br>AGTGTGTAATGATGCCTCCTGGGAGACTCGTTTTTATTGGCACAAGGGACTCCTGGGTCTGAGTA<br>ATGCAACAGTGGAATGGCATATTCCAGACACTGCCCAGCCTGGAATCTACAGAATAAGATATTTT<br>GGACACAATCGGAAGCAGGACATTCTGAAGCCTGCTGTCATACTTTCATTTGAAGGCACTTCCCC<br>GGCTTTTGAAGTTGTAACTATTTAGTGA (SEQ ID NO: 9) |
| ASAH2B<br>transcript<br>variant 1 | ATGAGGCAGCATCGACAATTTATGGACCGCACGCATTATCTGCTTACATTCAGCTCTTCAGAAACC<br>TTGCTAAGGCTATTGCTACGTATTGTGGATAGAGCACCAAAAGGCAGAACTTTCGGGGATGTCCT<br>GCAGCCAGCAAAACCTGAATACAGAGTGGGGGAAGTTGCTGAAGTTATATTTGTAGGTGCTAAC<br>CCGAAGAATTCAGTACAAAACCAGACCCATCAGACCTTCCTCACTGTGGAGAAATATGAGGCTAC<br>TTCAACATCGTGGCAGATAGTGTGTAATGATGCCTCCTGGGAGACTCGTTTTTATTGGCACAAGG<br>GACTCCTGGGTCTGAGTAATGCAACAGTGGAATGGCATATTCCAGACACTGCCCAGCCTGGAATC<br>TACAGAATAAGATATTTTGGACACAATCGGAAGCAGGACATTCTGAAGCCTGCTGTCATACTTTC<br>ATTTGAAGGCACTTCCCCGGCTTTTGAAGTTGTAACTATTTAGTGA (SEQ ID NO: 10) |
| ASAH 2B<br>transcript<br>variant 3 | ATGGTAGCCAACCTGAGCAGAGGTCCAGAACCTCCCTTTTTCAAACAATTAATAGTTCCATTAATT<br>CCTAGTATTGTGGATAGAGCACCAAAAGGCAGAACTTTCGGGGATGTCCTGCAGCCAGCAAAAC<br>CTGAATACAGAGTGGGGGAAGTTGCTGAAGTTATATTTGTAGGTGCTAACCCGAAGAATTCAGT<br>ACAAAACCAGACCCATCAGACCTTCCTCACTGTGGAGAAATATGAGGCTACTTCAACATCGTGGC<br>AGATAGTGTGTAATGATGCCTCCTGGGAGACTCGTTTTTATTGGCACAAGGGACTCCTGGGTCTG<br>AGTAATGCAACAGTGGAATGGCATATTCCAGACACTGCCCAGCCTGGAATCTACAGAATAAGATA<br>TTTTGGACACAATCGGAAGCAGGACATTCTGAAGCCTGCTGTCATACTTTCATTTGAAGGCACTTC<br>CCCGGCTTTTGAAGTTGTAACTATTTAGTGAATGGTAGCCAACCTGAGCAGAGGTCCAGAACCTC<br>CCTTTTTCAAACAATTAATAGTTCCATTAATTCCTAGTATTGTGGATAGAGCACCAAAAGGCAGAA<br>CTTTCGGGGATGTCCTGCAGCCAGCAAAACCTGAATACAGAGTGGGGGAAGTTGCTGAAGTTAT<br>ATTTGTAGGTGCTAACCCGAAGAATTCAGTACAAAACCAGACCCATCAGACCTTCCTCACTGTGG<br>AGAAATATGAGGCTACTTCAACATCGTGGCAGATAGTGTGTAATGATGCCTCCTGGGAGACTCGT<br>TTTTATTGGCACAAGGGACTCCTGGGTCTGAGTAATGCAACAGTGGAATGGCATATTCCAGACAC<br>TGCCCAGCCTGGAATCTACAGAATAAGATATTTTGGACACAATCGGAAGCAGGACATTCTGAAGC<br>CTGCTGTCATACTTTCATTTGAAGGCACTTCCCCGGCTTTTGAAGTTGTAACTATTTAGTGA<br>(SEQ ID NO: 11) |
| ASAH2B<br>transcript<br>variant 4 | ATGGTAGCCAACCTGAGCAGAGGTCCAGAACCTCCCTTTTTCAAACAATTAATAGTTCCATTAATT<br>CCTAGTATTGTGGATAGAGCACCAAAAGGCAGAACTTTCGGGGATGTCCTGCAGCCAGCAAAAC<br>CTGAATACAGAGTGGGGGAAGTTGCTGAAGTTATATTTGTAGGTGCTAACCCGAAGAATTCAGT<br>ACAAAACCAGACCCATCAGACCTTCCTCACTGTGGAGAAATATGAGGCTACTTCAACATCGTGGC<br>AGATAGTGTGTAATGATGCCTCCTGGGAGACTCGTTTTTATTGGCACAAGGGACTCCTGGGTCTG<br>AGTAATGCAACAGTGGAATGGCATATTCCAGACACTGCCCAGCCTGGAATCTACAGAATAAGATA<br>TTTTGGACACAATCGGAAGCAGGACATTCTGAAGCCTGCTGTCATACTTTCATTTGAAGGCACTTC<br>CCCGGCTTTTGAAGTTGTAACTATTTAG (SEQ ID NO: 12) |
| ACER1 | ATGCCTAGCATCTTCGCCTATCAGAGCTCCGAGGTGGACTGGTGTGAGAGCAACTTCCAGTACTC<br>GGAGCTGGTGGCCGAGTTCTACAACACGTTCTCCAATATCCCCTTCTTCATCTTCGGGCCACTGAT<br>GATGCTCCTGATGCACCCGTATGCCCAGAAGCGCTCCCGCTACATTTACGTTGTCTGGGTCCTCTT<br>CATGATCATAGGCCTGTTCTCCATGTATTTCCACATGACGCTCAGCTTCCTGGGCCAGCTGCTGGA<br>CGAGATCGCCATCCTGTGGCCTCCTGGGCAGTGGCTATAGCATATGGATGCCCCGCTGCTATTTCC<br>CCTCCTTCCTTGGGGGGAACAGGTCCCAGTTCATCCGCCTGGTCTTCATCACCACTGTGGTCAGCA<br>CCCTTCTGTCCTTCCTGCGGCCCACGGTCAACGCCTACGCCCTCAACAGCATTGCCCTGCACATTCT<br>CTACATCGTGTGCCAGGAGTACAGGAAGACCAGCAATAAGGAGCTTCGGCACCTGATTGAGGTC<br>TCCGTGGTTTTATGGGCTGTTGCTCTGACCAGCTGGATCAGTGACCGTCTGCTTTGCAGCTTCTGG<br>CAGAGGATTCATTTCTTCTATCTGCACAGCATCTGGCATGTGCTCATCAGCATCACCTTCCCTTATG<br>GCATGGTCACCATGGCCTTGGTGGATGCCAACTATGAGATGCCAGGTGAAACCCTCAAAGTCCGC<br>TACTGGCCTCGGGACAGTTGGCCCGTGGGGCTGCCCTACGTGGAAATCCGGGGTGATGACAAGG<br>ACTGCTGA (SEQ ID NO: 13) |
| ACER2 | ATGGGCGCCCCGCACTGGTGGGACCAGCTGCAGGCTGGTAGCTCGGAGGTGGACTGGTGCGAG<br>GACAACTACACCATCGTGCCTGCTATCGCCGAGTTCTACAACACGATCAGCAATGTCTTATTTTTC<br>ATTTTACCGCCCATCTGCATGTGCTTGTTTCGTCAGTATGCAACATGCTTCAACAGTGGCATCTACT<br>TAATCTGGACTCTTTTGGTTGTAGTGGGAATTGGATCCGTCTACTTCCATGCAACCCTTAGTTTCTT<br>GGGTCAGATGCTTGATGAACTTGCAGTCCTTTGGGTTCTGATGTGTGCTTTGGCCATGTGGTTCCC<br>CAGAAGGTATCTACCAAAGATCTTTCGGAATGACCGGGGTAGGTTCAAGGTGGTGGTCAGTGTC<br>CTGTCTGCGGTTACGACGTGCCTGGCATTTGTCAAGCCTGCCATCAACAACATCTCTCTGATGACC<br>CTGGGAGTTCCTTGCACTGCACTGCTCATCGCAGAGCTAAAGAGGTGTGACAACATGCGTGTGTT<br>TAAGCTGGGCCTCTTCTCGGGCCTCTGGTGGACCCTGGCCCTGTTCTGCTGGATCAGTGACCGAG<br>CTTTCTGCGAGCTGCTGTCATCCTTCAACTTCCCCTACCTGCCATGTGGCACATCCTCATCTG<br>CCTTGCTGCCTACCTGGGCTGTGTATGCTTTGCCTACTTTGATGCTGCCTCAGAGATTCCTGAGCA<br>AGGCCCTGTCATCAAGTTCTGGCCCAATGAGAAATGGGCCTTCATTGGTGTCCCCTATGTGTCCCT<br>CCTGTGTGCCAACAAGAAATCATCAGTCAAGATCACGTGA (SEQ ID NO: 14) |
| ACER3<br>transcript<br>variant 1 | ATGGCTCCGGCCGCGGACCGAGAGGGCTACTGGGGCCCCACGACCTCCACGCTGGACTGGTGCG<br>AGGAGAACTACCTCGTGACCTGGTACATCGCCGAGTTCTGGAATACAGTGAGTAACCTGATCATG<br>ATTATACCTCCAATGTTCGGTGCAGTTCAGAGTGTTAGAGACGGTCTGGAAAAGCGGTACATTGC<br>TTCTTATTTAGCACTCACAGTGGTAGGAATGGGATCCTGGTGCTTCCACATGACTCTGAAATATGA<br>AATGCAGCTATTGGATGAACTCCCAATGATATACAGCTGTTGCATATTTGTGTACTGCATGTTTGA |

TABLE 1-continued

| Gene | Open Reading Frame |
|---|---|
| | ATGTTTCAAGATCAAGAACTCAGTAAACTACCATCTGCTTTTTACCTTAGTTCTATTCAGTTTAATA<br>GTAACCACAGTTTACCTTAAGGTAAAAGAGCCGATATTCCATCAGGTCATGTATGGAATGTTGGT<br>CTTTACATTAGTACTTCGATCTATTTATATTGTTACATGGGTTTATCCATGGCTTAGAGGACTGGGT<br>TATACATCATTGGGTATATTTTATTGGGATTTTTATTTTGGAATATAGATAACATATTTTGTGAGT<br>CACTGAGGAACTTTCGAAAGAAGGTACCACCTATCATAGGTATTACCACACAATTTCATGCATGG<br>TGGCATATTTTAACTGGCCTTGGTTCCTATCTTCACATCCTTTTCAGTTTGTATACAAGAACACTTT<br>ACCTGAGATATAGGCCAAAAGTGAAGTTTCTCTTTGGAATCTGGCCAGTGATCCTGTTTGAGCCTC<br>TCAGGAAGCATTGA (SEQ ID NO: 15) |
| ACER3<br>transcript<br>variant 2 | ATGGCTCCGGCCGCGGACCGAGAGGGCTACTGGGGCCCCACGACCTCCACGCTGGACTGGTGCG<br>AGGAGAACTACTCCGTGACCTGGTACATCGCCGAGTTCTTGGTAGGAATGGGATCCTGGTGCTTC<br>CACATGACTCTGAAATATGAAATGCAGCTATTGGATGAACTCCCAATGATATACAGCTGTTGCAT<br>ATTTGTGTACTGCATGTTTGAATGTTTCAAGATCAAGAACTCAGTAAACTACCATCTGCTTTTTACC<br>TTAGTTCTATTCAGTTTAATAGTAACCACAGTTTACCTTAAGGTAAAAGAGCCGATATTCCATCAG<br>GTCATGTATGGAATGTTGGTCTTTACATTAGTACTTCGATCTATTTATATTGTTACATGGGTTTATC<br>CATGGCTTAGAGGACTGGGTTATACATCATTGGGTATATTTTATTGGGATTTTTATTTTGGAATA<br>TAGATAACATATTTTGTGAGTCACTGAGGAACTTTCGAAAGAAGGTACCACCTATCATAGGTATT<br>ACCACACAATTTCATGCATGGTGGCATATTTTAACTGGCCTTGGTTCCTATCTTCACATCCTTTTCA<br>GTTTGTATACAAGAACACTTTACCTGAGATATAGGCCAAAAGTGAAGTTTCTCTTTGGAATCTGGC<br>CAGTGATCCTGTTTGAGCCTCTCAGGAAGCATTGA (SEQ ID NO: 16) |
| ACER3<br>transcript<br>variant 3 | ATGATATACAGCTGTTGCATATTTGTGTACTGCATGTTTGAATGTTTCAAGATCAAGAACTCAGTA<br>AACTACCATCTGCTTTTTACCTTAGTTCTATTCAGTTTAATAGTAACCACAGTTTACCTTAAGGTAA<br>AAGAGCCGATATTCCATCAGGTCATGTATGGAATGTTGGTCTTTACATTAGTACTTCGATCTATTT<br>ATATTGTTACATGGGTTTATCCATGGCTTAGAGGACTGGGTTATACATCATTGGGTATATTTTAT<br>TGGGATTTTTATTTTGGAATATAGATAACATATTTTGTGAGTCACTGAGGAACTTTCGAAAGAAG<br>GTACCACCTATCATAGGTATTACCACACAATTTCATGCATGGTGGCATATTTTAACTGGCCTTGGT<br>TCCTATCTTCACATCCTTTTCAGTTTGTATACAAGAACACTTTACCTGAGATATAGGCCAAAAGTGA<br>AGTTTCTCTTTGGAATCTGGCCAGTGATCCTGTTTGAGCCTCTCAGGAAGCATTGA (SEQ ID NO:<br>17) |
| Sphk2 | ATGAATGGACACCTTGAAGCAGAGGAGCAGCAGGACCAGAGGCCAGACCAGGAGCTGACCGGG<br>AGCTGGGGCCACGGGCCTAGGAGCACCCTGGTCAGGGCTAAGGCCATGGCCCCGCCCCACCGC<br>CACTGGCTGCCAGCACCCCGCTCCTCCATGGCGAGTTTGGCTCCTACCCAGCCCGAGGCCCACGC<br>TTTGCCCTCACCCTTACATCGCAGGCCCTGCACATACAGCGGCTGCGCCCCAAACCTGAAGCCAG<br>GCCCCGGGGTGGCCTGGTCCCGTTGGCCGAGGTCTCAGGCTGCTGCACCCTGCGAAGCCGCAGC<br>CCCTCAGACTCAGCGGCCTACTTCTGCATCTACACCTACCCTCGGGGCCGGCGCGGGGCCCGGCG<br>CAGAGCCACTCGCACCTTCCGGGCAGATGGGGCCGCCACCTACGAAGAGAACCGTGCCGAGGCC<br>CAGCGCTGGGCCACTGCCCTCACCTGTCTGCTCCGAGGACTGCCACTGCCCGGGGATGGGGAGA<br>TCACCCCTGACCTGCTACCTCGGCCGCCCCGGTTGCTTCTATTGGTCAATCCCTTTGGGGGTCGGG<br>GCCTGGCCTGGCAGTGGTGTAAGAACCACGTGCTTCCCATGATCTCTGAAGCTGGGCTGTCCTTC<br>AACCTCATCCAGACAGAACGACAGAACCACGCCCGGGAGCTGGTCCAGGGGCTGAGCCTGAGTG<br>AGTGGGATGGCATCGTCACGGTCTCGGGAGACGGGCTGCTCCATGAGGTGCTGAACGGGCTCCT<br>AGATCGCCCTGACTGGGAGGAAGCTGTGAAGATGCCTGTGGGCATCCTCCCCTGCCGCTCGGGC<br>AACGCGCTGGCCGGAGCAGTGAACCAGCACGGGGGATTTGAGCCAGCCCTGGGCCTCGACCTGT<br>TGCTCAACTGCTCACTGTTGCTGTGCCGGGTGGTGGCCACCCACTGGACCTGCTCTCGTGACG<br>CTGGCCTCGGGCTCCCGCTGTTTCTCCTTCCTGTCTGTGGCCTGGGGCTTCGTGTCAGATGTGGAT<br>ATCCAGAGCGAGCGCTTCAGGGCCTTGGGCAGTGCCGGCTTCACACTGGGCACGGTGCTGGGCC<br>TCGCCACACTGCACACCTACCGCGGACGCCTCTCCTACCTCCCCGCCACTGTGGAACCTGCCTCGC<br>CCACCCCTGCCCATAGCCTGCCTCGTGCCAAGTCGGAGCTGACCCTAACCCCAGACCCAGCCCCG<br>CCCATGGCCCACTCACCCCTGCATCGTTCTGTGTCTGACCTGCCTCTTCCCCTGCCCCAGCCTGCCC<br>TGGCCTCTCCTGGCTCGCCAGAACCCCTGCCCATCCTGTCCCTCAACGGTGGGGGCCCAGAGCTG<br>GCTGGGGACTGGGGTGGGGCTGGGGATGCTCCGCTGTCCCCGGACCCACTGCTGTCTTCACCTC<br>CTGGCTCTCCCAAGGCAGCTCTACACTCACCCGTCTCCGAAGGGGCCCCGTAATTCCCCCATCCT<br>CTGGGCTCCCACTTCCCACCCCTGATGCCCGGGTAGGGGCCTCCACCTGCGGCCCGCCCGACCAC<br>CTGCTGCCTCCGCTGGGCACCCCCGCTGCCCCCAGACTGGGTGACCTGGAGGGGGACTTTGTGC<br>TCATGTTGGCCATCTCGCCCAGCCACCTAGGCGCTGACCTGGTGGCAGCTCCGCATGCGCGCTTC<br>GACGACGGCCTGGTGCACCTGTGCTGGGTGCGTAGCGGCATCTCGCGGGCTGCGCTGCTGCGCC<br>TTTTCTTGGCCATGGAGCGTGGTAGCCACTTCAGCCTGGGCTGTCCGCAGCTGGGCTACGCCGCG<br>GCCCGTGCCTTCCGCCTAGAGCCGCTCACACCACGCGGCGTGCTCACAGTGGACGGGGAGCAGG<br>TGGAGTATGGGCCGCTACAGGCACAGATGCACCCTGGCATCGGTACACTGCTCACTGGGCCTCCT<br>GGCTGCCCGGGGCGGGAGCCCTGA (SEQ ID NO: 18) |
| CerK | ATGGGGGCGACGGGGGCGGCGGAGCCGCTGCAATCCGTGCTGTGGGTGAAGCAGCAGCGCTGC<br>GCCGTGAGCCTGGAGCCCGCGGGGCTCTGCTGCGCTGGTGGCGGAGCGGGGCCCGAGCC<br>GGCGCCCCGGCGCGGATGCCTGCTCTGTGCCTGTATCGAGATCATCGCCGTTGAGGAAACAG<br>ACGTTCACGGGAAACATCAAGGCAGTGGAAATGCAGAAAATGGAAAAGCCTTACGCTTTTAC<br>AGTTCACTGTGTAAAGAGAGCACGACGGCACCGCTGGAAGTGGGCGCAGGTGACTTTCTGGTGT<br>CCAGAGGAGCAGCTGTGTCACTGTGGCTGCAGACCCTGCGGGAGATGCTGGAGAAGCTGACGT<br>CCAGACCAAAGCATTTACTGGTATTTATCAACCCGTTTGGAGGAAAAGGACAAGGCAAGCGGAT<br>ATATGAAAGAAAGTGGCACCACTGTTCACCTTAGCCTCCATCACCACTGACATCATCGTTACTGA<br>ACATGCTAATCAGGCCAAGGAGACTCTGTATGAGATTAACATAGACAAATACGACGGCATCGTCT<br>GTGTCGGCGGAGATGGTATGTTCAGCGAGGTGCTGCACGGTCTGATTGGGAGGACGCAGAGGA<br>GCGCCGGGGTCGACCAGAACCACCCCCGGGCTGTCTGGTCCCAGTAGCCTCCGGATTGGAAT<br>CATTCCCGCAGGGTCAACGGACTGCGTGTTACTCCACCGTGGGCACCAGCGACGCAGAAACCT<br>CGGCGCTGCATATCGTTGTTGGGGACTCGCTGGCCATGGATGTGTCCTCAGTCCACCACAACAGC<br>ACACTCCTTCGCTACTCCGTGTCCCTGCTGGGCTACGGCTTCTACGGGGACATCATCAAGGACAG<br>TGAGAAGAAACGGTGGTTGGGTCTTGCCAGATACGACTTTTCAGGTTTAAAGACCTTCCTCTCCC |

TABLE 1-continued

| Gene | Open Reading Frame |
|---|---|
| | ACCACTGCTATGAAGGGACAGTGTCCTTCCTCCCTGCACAACACACGGTGGGATCTCCAAGGGAT<br>AGGAAGCCCTGCCGGGCAGGATGCTTTGTTTGCAGGCAAAGCAAGCAGCAGCTGGAGGAGGAG<br>CAGAAGAAAGCACTGTATGGTTTGGAAGCTGCGGAGGACGTGGAGGAGTGGCAAGTCGTCTGT<br>GGGAAGTTTCTGGCCATCAATGCCACAAACATGTCCTGTGCTTGTCGCCGGAGCCCCAGGGGCCT<br>CTCCCCGGCTGCCCACTTGGGAGACGGGTCTTCTGACCTCATCCTCATCCGGAAATGCTCCAGGTT<br>CAATTTTCTGAGATTTCTCATCAGGCACACCAACCAGCAGGACCAGTTTGACTTCACTTTTGTTGA<br>AGTTTATCGCGTCAAGAAATTCCAGTTTACGTCGAAGCACATGGAGGATGAGGACAGCGACCTC<br>AAGGAGGGGGGAAGAAGCGCTTTGGGCACATTTGCAGCAGCCACCCCTCCTGCTGCTGCACCG<br>TCTCCAACAGCTCCTGGAACTGCGACGGGGAGGTCCTGCACAGCCCTGCCATCGAGGTCAGAGT<br>CCACTGCCAGCTGGTTCGACTCTTTGCACGAGGAATTGAAGAGAATCCGAAGCCAGACTCACACA<br>GCTGA<br>(SEQ ID NO: 19) |

EXAMPLES

Mice

All animal procedures were performed under protocols approved by the Icahn School of Medicine at Mount Sinai Institutional Care and Use Committee.

Synthesis of Anc80.AC

The nucleotide sequence for an embodiment of the Anc80 plasmid described herein is shown below. A map of the vector is also shown in FIG. 16.

Anc80 Plasmid Sequence

| pAAV.CMV.<br>WPRE.bGH.dna | CTGCGCGCTCGCTCGCTCACTGAGGCCGCCCGGGCAAAGCCCGGGCGTCG<br>GGCGACCTTTGGTCGCCCGGCCTCAGTGAGCGAGCGAGCGCGCAGAGAGG<br>GAGTGGCCAACTCCATCACTAGGGGTTCCTTGTAGTTAATGATTAACCCGCC<br>ATGCTACTTATCTACGTAGCCATGCTCTAGGAAGATCGGAATTCGCCCTTAAG<br>CTAGCTAGTTATTAATAGTAATCAATTACGGGGTCATTAGTTCATAGCCCATAT<br>ATGGAGTTCCGCGTTACATAACTTACGGTAAATGGCCCGCCTGGCTGACCGC<br>CCAACGACCCCCGCCCATTGACGTCAATAATGACGTATGTTCCCATAGTAAC<br>GCCAATAGGGACTTTCCATTGACGTCAATGGGTGGAGTATTTACGGTAAACT<br>GCCCACTTGGCAGTACATCAAGTGTATCATATGCCAAGTACGCCCCCTATTG<br>ACGTCAATGACGGTAAATGGCCCGCCTGGCATTATGCCCAGTACATGACCTT<br>ATGGGACTTTCCTACTTGGCAGTACATCTACGTATTAGTCATCGCTATTACCA<br>TGGTGATGCGGTTTTGGCAGTACATCAATGGGCGTGGATAGCGGTTTGACTC<br>ACGGGGATTTCCAAGTCTCCACCCCATTGACGTCAATGGGAGTTTGTTTTGG<br>CACCAAAATCAACGGGACTTTCCAAAATGTCGTAACAACTCCGCCCCATTGAC<br>GCAAATGGGCGGTAGGCGTGTACGGTGGGAGGTCTATATAAGCAGAGCTGG<br>TTTAGTGAACCGTCAGATCCTGCAGAAGTTGGTCGTGAGGCACTGGGCAGGT<br>AAGTATCAAGGTTACAAGACAGGTTTAAGGAGACCAATAGAAACTGGGCTTG<br>TCGAGACAGAGAAGACTCTTGCGTTTCTGATAGGCACCTATTGGTCTTACTGA<br>CATCCACTTTGCCTTTCTCTCCACAGGTGTCCAGGCGGCCGCNNNGGATCCA<br>ATCAACCTCTGGATTACAAAATTTGTGAAAGATTGACTGGTATTCTTAACTATG<br>TTGCTCCTTTTACGCTATGTGGATACGCTGCTTTAATGCCTTTGTATCATGCTA<br>TTGCTTCCCGTATGGCTTTCATTTTCTCCTCCTTGTATAAATCCTGGTTGCTGT<br>CTCTTTATGAGGAGTTGTGGCCCGTTGTCAGGCAACGTGGCGTGGTGTGCAC<br>TGTGTTTGCTGACGCAACCCCCACTGGTTGGGGCATTGCCACCACCTGTCAG<br>CTCCTTTCCGGGACTTTCGCTTTCCCCCTCCCTATTGCCACGGCGGAACTCA<br>TCGCCGCCTGCCTTGCCCGCTGCTGGACAGGGGCTCGGCTGTTGGGCACTG<br>ACAATTCCGTGGTGTTGTCGGGGAAATCATCGTCCTTTCCTTGGCTGCTCGC<br>CTGTGTTGCCACCTGGATTCTGCGCGGGACGTCCTTCTGCTACGTCCCTTCG<br>GCCCTCAATCCAGCGGACCTTCCTTCCCGCGGCCTGCTGCCGGCTCTGCGG<br>CCTCTTCCGCGTCTTCGAGATCTGCCTCGACTGTGCCTTCTAGTTGCCAGCC<br>ATCTGTTGTTTGCCCCTCCCCGTGCCTTCTTGACCCTGGAAGGTGCCACT<br>CCCACTGTCCTTTCCTAATAAAATGAGGAAATTGCATCGCATTGTCTGAGTAG<br>GTGTCATTCTATTCTGGGGGGTGGGGTGGGGCAGGACAGCAAGGGGGAGG<br>ATTGGGAAGACAATAGCAGGCATGCTGGGGACTCGAGTTAAGGGCGAATTC<br>CCGATAAGGATCTTCCTAGAGCATGGCTACGTAGATAAGTAGCATGGCGGGT<br>TAATCATTAACTACAAGGAACCCCTAGTGATGGAGTTGGCCACTCCCTCTCTG<br>CGCGCTCGCTCGCTCACTGAGGCCGGGCGACCAAAGGTCGCCCGACGCCC<br>GGGCTTTGCCCGGGCGGCCTCAGTGAGCGAGCGAGCGCGCAGCCTTAATTA<br>ACCTAATTCACTGGCCGTCGTTTTACAACGTCGTGACTGGGAAAACCCTGGC<br>GTTACCCAACTTAATCGCCTTGCAGCACATCCCCCTTTCGCCAGCTGGCGTA<br>ATAGCGAAGAGGCCCGCACCGATCGCCCTTCCCAACAGTTGCGCAGCCTGA<br>ATGGCGAATGGGACGCGCCCTGTAGCGGCGCATTAAGCGCGGCGGGTGTG<br>GTGGTTACGCGCAGCGTGACCGCTACACTTGCCAGCGCCCTAGCGCCCGCT<br>CCTTTCGCTTTCTTCCCTTCCTTTCTCGCCACGTTCGCCGGCTTTCCCCGTCA<br>AGCTCTAAATCGGGGGCTCCCTTTAGGGTTCCGATTTAGTGCTTTACGGCAC<br>CTCGACCCCAAAAAACTTGATTAGGGTGATGGTTCACGTAGTGGGCCATCGC<br>CCTGATAGACGGTTTTTCGCCCTTTGACGTTGGAGTCCACGTTCTTTAATAGT<br>GGACTCTTGTTCCAAACTGGAACAACACTCAACCCTATCTCGGTCTATTCTTT<br>TGATTTATAAGGGATTTTGCCGATTTCGGCCTATTGGTTAAAAAATGAGCTGA<br>TTTAACAAAAATTTAACGCGAATTTTAACAAAATATTAACGTTTATAATTTCAGG<br>TGGCATCTTTCGGGGAAATGTGCGCGGAACCCCTATTTGTTTATTTTTCTAAA<br>TACATTCAAATATGTATCCGCTCATGAGACAATAACCCTGATAAATGCTTCAAT<br>AATATTGAAAAAGGAAGAGTATGAGTATTCAACATTTCCGTGTCGCCCTTATT |

-continued

```
CCCTTTTTTGCGGCATTTTGCCTTCCTGTTTTTGCTCACCCAGAAACGCTGGT
GAAAGTAAAAGATGCTGAAGATCAGTTGGGTGCACGAGTGGGTTACATCGAA
CTGGATCTCAATAGTGGTAAGATCCTTGAGAGTTTTCGCCCCGAAGAACGTTT
TCCAATGATGAGCACTTTTAAAGTTCTGCTATGTGGCGCGGTATTATCCCGTA
TTGACGCCGGGCAAGAGCAACTCGGTCGCCGCATACACTATTCTCAGAATGA
CTTGGTTGAGTACTCACCAGTCACAGAAAAGCATCTTACGGATGGCATGACA
GTAAGAGAATTATGCAGTGCTGCCATAACCATGAGTGATAACACTGCGGCCA
ACTTACTTCTGACAACGATCGGAGGACCGAAGGAGCTAACCGCTTTTTTGCA
CAACATGGGGATCATGTAACTCGCCTTGATCGTTGGGAACCGGAGCTGAAT
GAAGCCATACCAAACGACGAGCGTGACACCACGATGCCTGTAGTAATGGTAA
CAACGTTGCGCAAACTATTAACTGGCGAACTACTTACTCTAGCTTCCCGGCAA
CAATTAATAGACTGGATGGAGGCGGATAAAGTTGCAGGACCACTTCTGCGCT
CGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCC
GTATCGTAGTTATCTACACGACGGGGAGTCAGGCAACTATGGATGAACGAAA
TAGACAGATCGCTGAGATAGGTGCCTCACTGATTAAGCATTGGTAACTGTCA
GACCAAGTTTACTCATATATACTTTAGATTGATTTAAAACTTCATTTTTAATTTA
AAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTT
TCCGAAGGTAACTGGCTTCAGCAGAGCGCAGATACCAAATACTGTCCTTCTA
GTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGA
CCTACACCGAACTGAGATACCTACAGCGTGAGCTATGAGAAAGCGCCACGCT
TCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGCTC
GTCAGGGGGCGGAGCCTATGGAAAAACGCCAGCAACGCGGCCTTTTTACG
GTTCCTGGCCTTTTGCTGCGGTTTTGCTCACATGTTCTTTCCTGCGTTATCCC
CTGATTCTGTGGATAACCGTATTACCGCCTTTGAGTGAGCTGATACCGCTCG
CCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATG
CAGCTGGCACGACAGGTTTCCCGACTGGAAAGCGGGCAGTGAGCGCAACGC
AATTAATGTGAGTTAGCTCACTCATTAGGCACCCCAGGCTTTACACTTTATGC
TTCCGGCTCGTATGTTGTGTGGAATTGTGAGCGGATAACAATTTCACACAGG
AAACAGCTATGACCATGATTACGCCAGATTTAATTAAGG (SEQ ID NO: 20)
```

Total RNA was isolated using the RNeasy mini kit (QIAGEN) and reverse transcribed using Superscript III reverse transcriptase (Invitrogen), according to the manufacturer's instructions. Real-time qPCR analyses were performed on a Mastercycler realplex 4 Sequence Detector (Eppendorf) using SYBR Green (Quantitect™ SYBR Green PCR Kit, QIAGEN). Data were normalized to 18srRNA expression where appropriate (endogenous controls). Fold changes of gene expression were determined by the ddCT method. PCR primer sequences are summarized in Table 2.

Western Blot

Upon thawing, hearts lysates' were subjected to separation by SDS-PAGE using 12% precast Nupage Bis/Tris gels (Invitrogen, Carlsbad, Calif., USA) under reducing conditions and MES running buffer (Invitrogen), and transferred onto a nitrocellulose membrane (Bio-Rad) using a semidry transfer apparatus and Nupage-MOPS transfer buffer (Invitrogen). The membrane was block with TBS/Tween containing 5% dry milk and incubated with specific primary antibodies over night at 4° C. washed with TBS/Tween and

TABLE 2

| Gene | Forward | SEQ ID NO. | Reverse | SEQ ID NO. |
| --- | --- | --- | --- | --- |
| AC | ACAGGATTCAAACCAGGACTGT | 21 | TGGGCATCTTTCCTTCCGAA | 22 |
| AC | TGACAGGATTCAAACCAGGACT | 23 | CTGGGCATCTTTCCTTCCGA | 24 |
| Sphk1 | ATACTCACCGAACGGAAGAACC | 25 | CCATTAGCCCATTCACCACCTC | 26 |
| Sphk1 | ACTGATACTCACCGAACGGAA | 27 | CATTAGCCCATTCACCACCTC | 28 |
| S1PR2 | CACAGCCAACAGTCTCCAAA | 29 | TCTGAGTATAAGCCGCCCA | 30 |
| S1PR2 | ATAGACCGAGCACAGCCAA | 31 | GAACCTTCTCAGGATTGAGGT | 32 |
| 18s rRNA* | TAACGAACGAGACTCTGGCAT | 33 | CGGACATCTAAGGGCATCACAG | 34 |

*Genetic Vaccines and Therapy 2004, 2:5 incubated with rabbit or goat antibodies conjugated to horseradish peroxidase for 1 hour at room temperature. Detection was performed by an enhanced chemiluminescence (ECL) detection system (Pierce, Rockford, Ill.). For molecular weight determination prestained protein standards (Amersham, Buckinghamshire, UK) were used.

Immunohistochemistry

The mouse hearts were harvested and perfused using perfusion buffer (2 g/l butanedione, monoxime and 7.4 g/l KCl in PBS×1) and 4% paraformaldehyde (PFA). Hearts were fixed in 4% PFA/PBS overnight on shaker and then washed with PBS for 1 hr and incubated in 30% sucrose/PBS at 40 C overnight. Before freezing, hearts were mounted in OCT for 30 min and frozen at −80° C. Transverse heart sections of 10 µM were made by cryostat. Cryosections were washed in PBST and blocked for 1 h with 5% donkey serum in PBST. Sections were incubated over night at 4° C. using primary antibodies for Troponin I, Sphk1, S1p2. Secondary antibodies were used for fluorescent labeling (Jackson ImmunoResearch Laboratories). TUNEL staining was performed according to manufacturer's recommendations (In-Situ Cell Death Detection Kit, Fluorescein, Cat#11684795910, Roche). Stained sections were imaged using a Zeiss Slide Scanner Axio Scan or Zeiss mic. Quantification of TUNEL in cardiac sections was performed using ImageJ software. For cell immunocytochemistry, Hek293 and isolated CMs were fixed on coverslips with 4% PFA for 10 min at room temperature. Following permeabilization with 0.1% TRITON® X100 in PBS for 10 min at room temperature, cells were blocked with 5% Donkey serum+0.1% TRITON® X100 in PBS for 30 minutes. Coverslips were incubated with primary antibodies in humidity chamber for 1 hour at room temperature followed by incubation with corresponding secondary antibodies conjugated to Alexa Fluor 488, Alexa Fluor 647 and Alexa Fluor 555, and Hoechst 33342 staining for nuclei visualization (all from Invitrogene). The fluorescent images were taken on a Zeiss fluorescent microscope at 20× magnification.

Model of PAH

A rat PAH model was used. Pneumonectomy combined with Sugen rat model results in fast pulmonary vascular remodeling comparable to clinical PAH and development of the plexiform lesions found in human PAH. AC gene was introduced using Anc80 as viral vector to the lung via intratracheal transfer.

Cardiovascular Evaluation

MRI was used to assess the effect of Anc80-AC on heart function and PAH parameters (right ventricular hemodynamics including ejection fraction, hypertrophy, pulmonary artery pressure and vascular resistance).

Tissue Evaluation

Animal tissues from Sprague-Dawley rats will be analyzed for RNA sequencing, proteomics and sphingolipids quantification.

Study groups: 1. No Anc80/AC no PAH; 2. Saline+PAH; 3. Anc80 only+PAH; 4. Anc80/AC, No PAH; 5. Anc80/AC+PAH.

Preliminary Results

Figure 2:
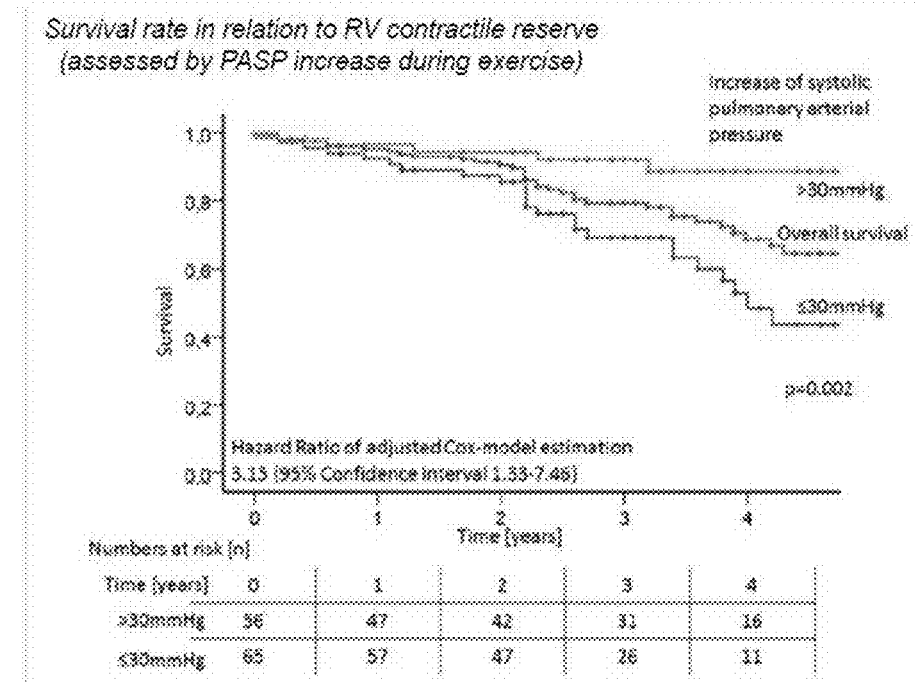
FIG. 2 is a graph showing that right ventricle (RV) function predicts mortality in PAH.
Figure 3:
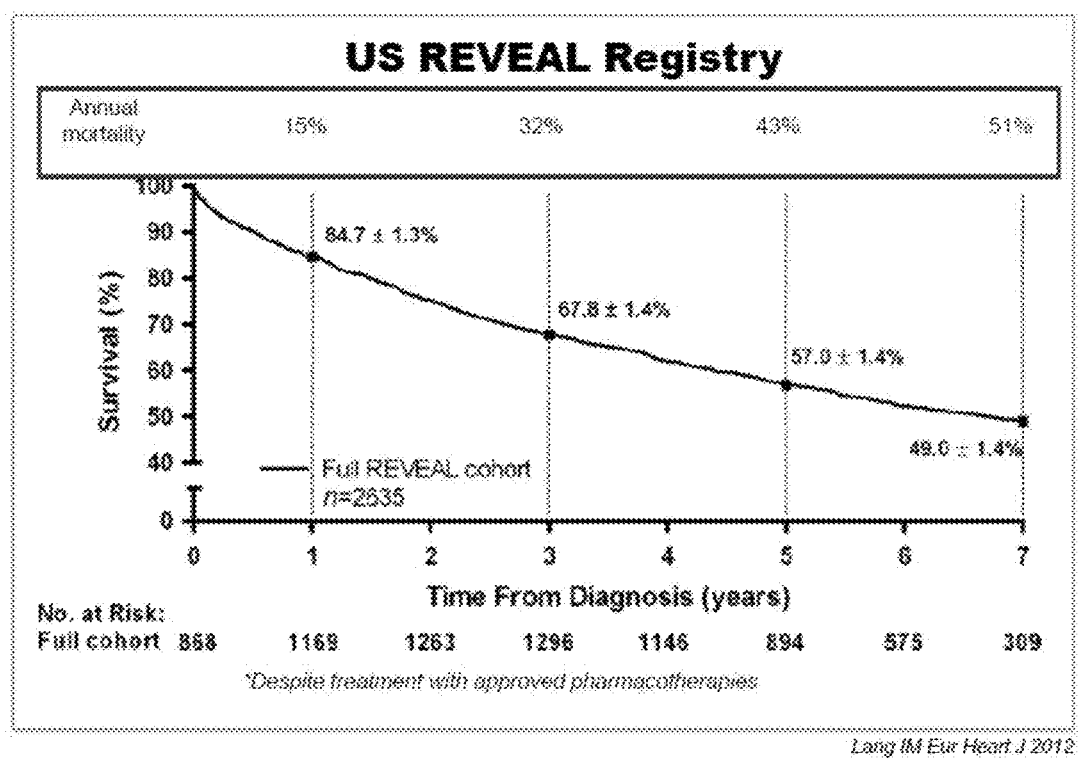
FIG. 3 shows seven year survival estimates of patients in the REVEAL registry. The REVEAL Registry is a multi-center, observational, U.S.-based study of the clinical course and disease management of PAH.
Figure 4:
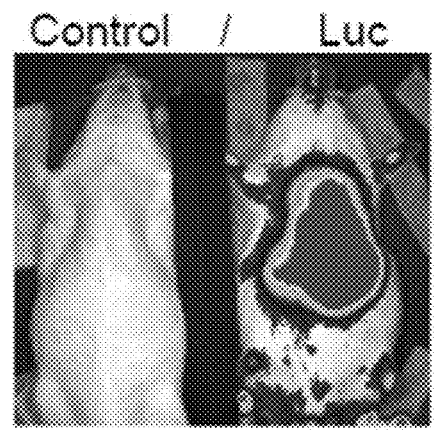
FIG. 4 shows biodistribution of Anc80 in a rat model. Rats were injected with Anc80 encoding luciferase. 72 hours post injection luciferase activity was assessed using IVIS machine.
Figure 5:
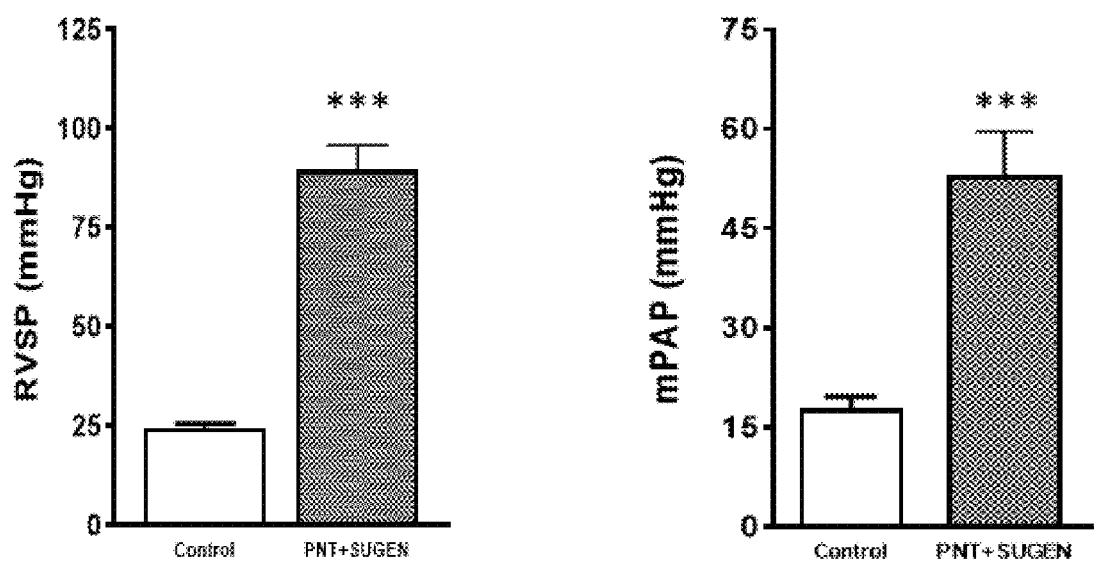
FIG. 5 shows severe pulmonary artery hypertension (PAH) in the left pneumonectomy combined with Sugen rat model. In this model right ventricular systolic pressure and mean pulmonary artery pressure significantly increased after 6 weeks.
Figures 6A, 6B, 6C:
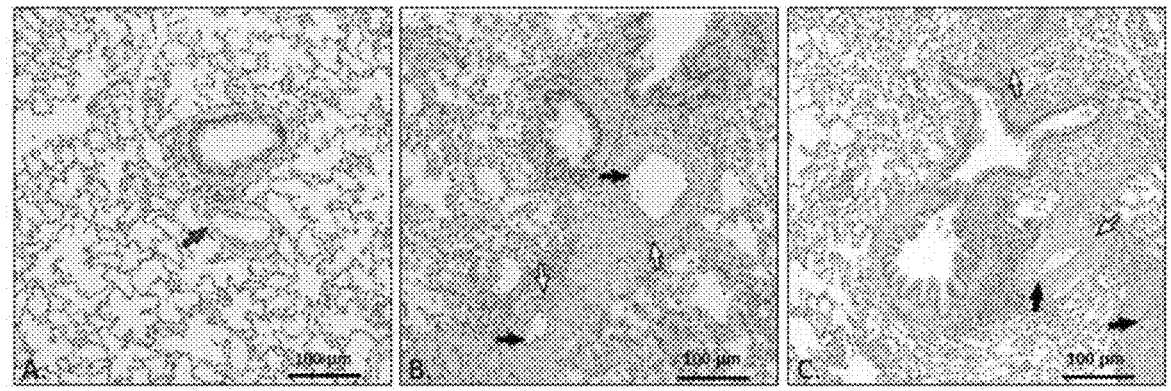
FIG. 6A-6C shows photomicrographs of hematoxylin and eosin (H&E) staining of lung tissue in PAH. Representative photomicrographs of H&E staining of lung tissue. A Normal lung. B-C Pathological vascular remodeling in PAH rats (pneumonectomy and Sugen). The lung shows concentric medial and intimal thickening (white and black arrows) and severe constricted pulmonary vessels.
Figure 7:
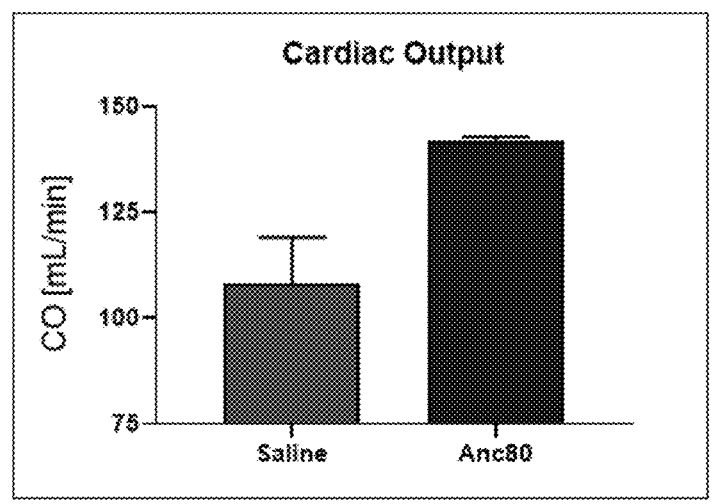
FIG. 7 shows hemodynamic data after Anc80 AC intratracheal injection. Rats were subjected to PAH induction protocol. On day 0, rats were subjected to baseline MRI, RV and PA catheterization to measure the pressure, and left lung removal. On day 7, pneumonectomized rats were subjected to SU5416 (Su/Pn 10 mg/kg) administration (SC injection). Induced animals demonstrated severely elevated mean PA pressures and developed neointima and smooth muscle hypertrophy. At week 4, PAH induced rats were treated with Anc80 AC ($1\times10^{11}$ genome copies). At week 6 and 8, animals were validated by MRI for heart function and RV and PA catheterization for pressure measurement. Treated animals with AC Anc80 at 8 weeks showed excellent cardiac function (validated by MRI) and normal PA pressures despite PAH disease present. After AC administration cardiac output increased 32%.
Figure 8:
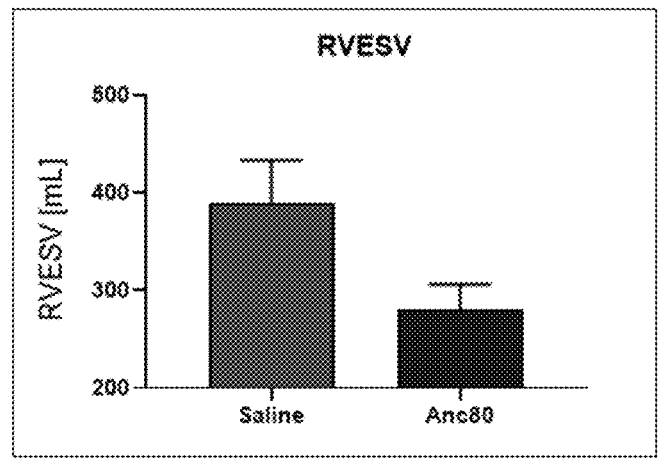
FIG. 8 shows hemodynamic data after Anc80 AC intratracheal injection. Rats were subjected to PAH induction protocol. On day 0 rats were subjected to baseline MRI, RV and PA catheterization to measure the pressure, and Left lung removal. On day 7, pneumonectomized rats were subjected to SU5416 (Su/Pn 10 mg/kg) administration (SC injection). Induced animals demonstrated severely elevated mean PA pressures and developed neointima and smooth muscle hypertrophy. At week 4, PAH induced rats were treated with Anc80 AC ($1\times10^{11}$ genome copies). At week 6 and 8, animals were validated by MRI for heart function and RV and PA catheterization for pressure measurement. After AC administration right ventricular systolic volume decreased 39%.

Rats were subjected to PAH induction protocol (FIG. 2). At week 0, rats were subjected to baseline MRI, RV and PA catheterization to measure the pressure, followed by left lung removal. On day 7 pneumonectomized rats were subjected to SU5416 (Su/Pn 10 mg/kg) administration (SC injection). Induced animals demonstrated severely elevated mean PA pressures and developed neointima and smooth muscle hypertrophy (FIGS. 3 and 4). On week 4 PAH induced rats were treated with Anc80 AC ($1\times10^{11}$ genome copies). On weeks 6 and 8 animals were validated by MRI for heart function and RV and PA catheterization for pressure measurement.

Figure 9:
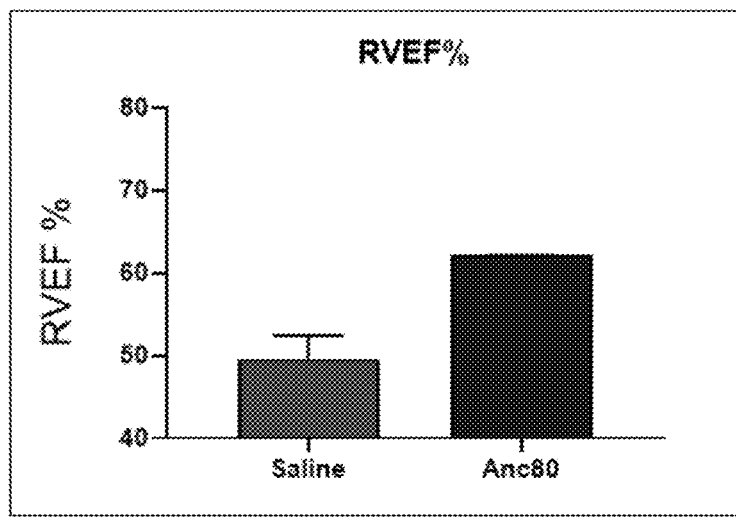
FIG. 9 shows hemodynamic data after Acn80 AC intratracheal injection. Rats were subjected to PAH induction protocol. On week 0 Rat were subjected to baseline MRI, RV and PA catheterization to measure the pressure, and Left lung removal. On day 7 pneumonectomized rats were subjected to SU5416 (Su/Pn 10 mg/kg) administration (SC injection). Induced animals demonstrated severely elevated mean PA pressures and develop neointima and smooth muscle hypertrophy. On week 4 PAH induced rats were treated with Anc80 AC ($1 \times 10^{11}$ genome copies). On week 6 and 8 animal were validated by MRI for heart function and RV and PA catheterization for pressure measurement. After AC administration right ventricular ejection fraction increased in 65%.
Figure 10:
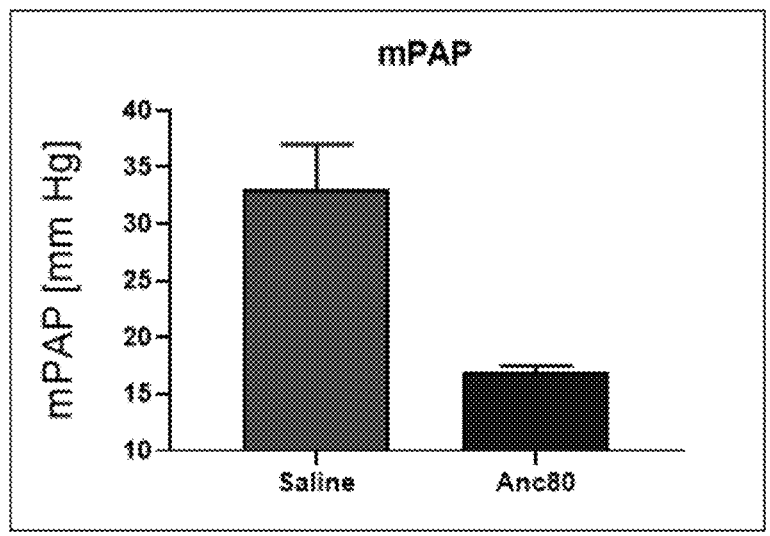
FIG. 10 shows hemodynamic data after Anc80 AC intra-tracheal injection. Rat were subjected to PAH induced protocol. On week 0 Rat were subjected to baseline MRI, RV and PA catheterization to measure the pressure, and Left lung removal. On day 7 pneumonectomized rats were subjected to SU5416 (Su/Pn 10 mg/kg) administration (SC injection). Induced animals demonstrated severely elevated mean PA pressures and develop neointima and smooth muscle hypertrophy. On week 4 PAH induced rats were treated with Anc80 AC ($1 \times 10^{11}$ genome copies). On week 6 and 8 animal were validated by MRI for heart function and RV and PA catheterization for pressure measurement. After AC administration mean pulmonary artery pressure decreased 94%.
Figure 11:
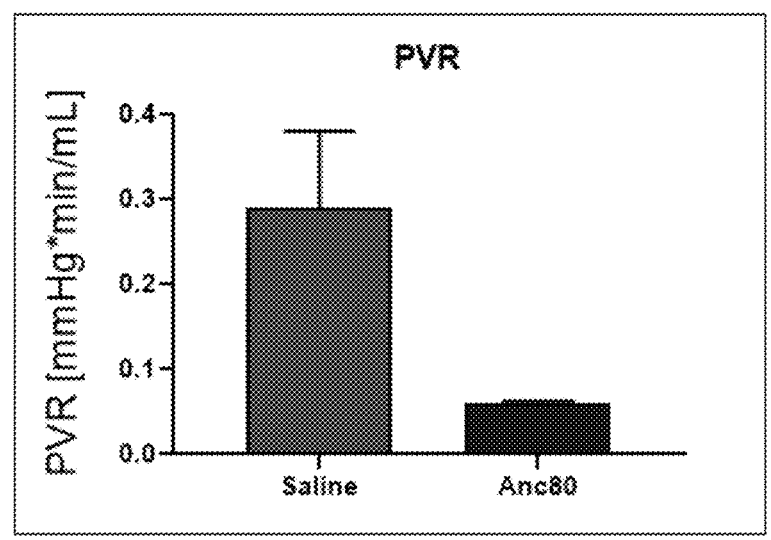
FIG. 11 shows hemodynamic data after Anc80 AC intra-tracheal injection. Rat were subjected to PAH induce protocol. On week 0 Rat were subjected to baseline MRI, RV and PA catheterization to measure the pressure, and Left lung removal. On day 7 pneumonectomized rats were subjected to SU5416 (Su/Pn 10 mg/kg) administration (SC injection). Induced animals demonstrated severely elevated mean PA pressures and develop neointima and smooth muscle hypertrophy. On week 4 PAH induced rats were treated with Anc80 AC ($1 \times 10^{11}$ genome copies). On week 6 and 8 animal were validated by MRI for heart function and RV and PA catheterization for pressure measurement. After AC administration mean pulmonary vascular resistance decreased 4.8 times.
Figure 12:
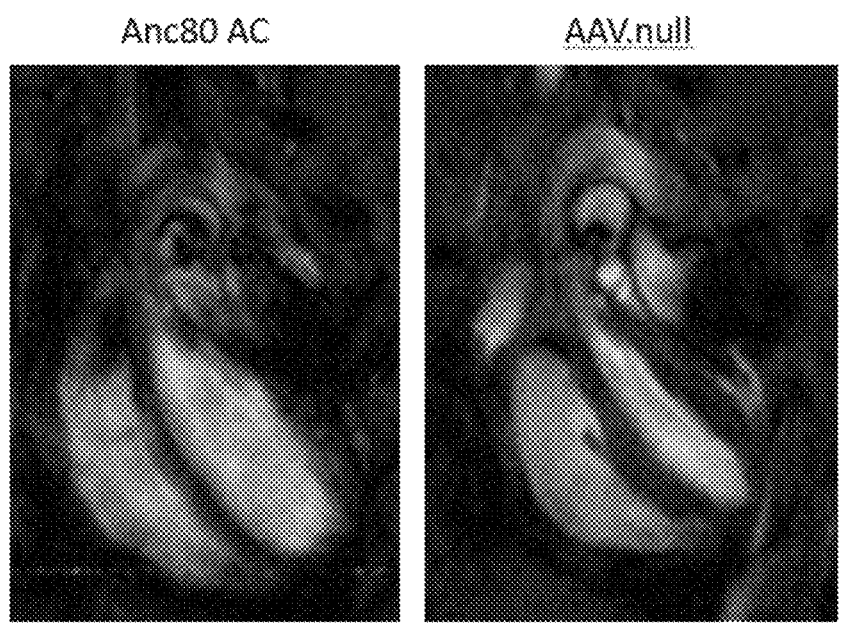
FIG. 12 shows MRI images showing heart function after Anc80 AC intra-tracheal injection. Rats were subjected to PAH induction protocol. On week 0, rats were subjected to baseline MRI, RV and PA catheterization to measure the pressure, and left lung removal. On day 7, pneumonectomized rats were subjected to SU5416 (Su/Pn 10 mg/kg) administration (SC injection). Induced animals demonstrated severely elevated mean PA pressures and developed neointima and smooth muscle hypertrophy. On week 4, PAH-induced rats were treated with Anc80 AC ($1 \times 10^{11}$ genome copies). On week 6 and 8, animals were evaluated by MRI for heart function and RV and PA catheterization for pressure measurement. Animals treated with Anc80 AC at 8 weeks showed excellent cardiac function.

Preliminary PAH results with AC-Anc80 gene therapy were outstanding (see FIGS. 5-10). In control animals a severe PAH develops after SU5416 (Su/Pn) administration to pneumonectomized rats. Induced animals demonstrated severely elevated mean PA pressures and developed neointima and smooth muscle hypertrophy. After AC administration cardiac output increased in 32% (FIG. 5), right ventricular systolic volume decreased in 39% (FIG. 6), right ventricular ejection fraction increased in 65% (FIG. 7), mean pulmonary artery pressure decreased in 94% (FIG. 8) and mean pulmonary vascular resistance decreased in 4.8 times (FIG. 9). Animals treated with AC Anc80 at 8 weeks showed excellent cardiac function (validated by MRI, FIG. 10) and normal PA pressures despite PAH disease present. In one embodiment, ancestral 80 (Anc80) viral vector was used for gene delivery. Anc80 has been used as a viral vector with low immunogenicity and ancestral strains that are not regularly recognized by human antibodies, unlike common AAVs that are seropositive in >50% of the population. Anc80 delivery has provided rapid onset of expression in less than 48 hours. The Anc80 virus demonstrated the ability to generate very high transduction of lung and other cardiovascular tissues. Overall, the Anc80 viral vector provided an ideal delivery vehicle for the gene.

It is to be understood that, while the methods and compositions of matter have been described herein in conjunction with a number of different aspects, the forgoing description of the various aspects is intended to illustrate and not limit the scope of the methods and compositions of matter. Other aspects, advantages, and modifications are within the scope of the following claims.

REFERENCES

Perez G I, Tao X J, Tilly J L. Fragmentation and death (a.k.a. apoptosis) of ovulated oocytes. Mol Hum Reprod. 1999; 5(5):414-20.

Eliyahu E, Park J H, Shtraizent N, He X, Schuchman E H. Acid ceramidase is a novel factor required for early embryo survival. FASEB J. 2007; 21(7):1403-9.

Eliyahu E, Shtraizent N, Martinuzzi K, Barritt J, He X, Wei H, Chaubal S, Copperman A B, Schuchman E H. Acid ceramidase improves the quality of oocytes and embryos and the outcome of in vitro fertilization. FASEB J. 2010, 24(4):1229-38.

Katalin Karikó, Hiromi Muramatsu, Frank A Welsh, János Ludwig, Hiroki Kato, Shizuo Akira, Drew Weissman. Incorporation of Pseudouridine Into mRNA Yields Superior Nonimmunogenic Vector With Increased Translational Capacity and Biological Stability. Mol Ther. 2008; 16(11): 1833-1840.

Yang H, Wang H, Shivalila C S, Cheng A W, Shi L, Jaenisch R. One-step generation of mice carrying reporter and conditional alleles by CRISPR/Cas-mediated genome engineering. Cell. 2013; 154(6): 1370-9.

Wu Y, Liang D, Wang Y, Bai M, Tang W, Bao S, Yan Z, Li D, Li J. Correction of a genetic disease in mouse via use of CRISPR-Cas9. Cell Stem Cell. 2013; 13(6):659-62.

Ruzo A, Brivanlou A H. At Last: Gene Editing in Human Embryos to Understand Human Development. Cell Stem Cell. 2017; 21(5):564-565.

Frumkin T, Peleg S, Gold V, Reches A, Asaf S, Azem F, Ben-Yosef D, Malcov M. Complex chromosomal rearrangement—a lesson learned from PGS. J Assist Reprod Genet. 2017; 34(8): 1095-1100.

Zinn et al. In *Silico Reconstruction of the Viral Evolutionary Lineage Yields a Potent Gene Therapy Vector, Cell Reports* 12.1056-1068 (2015)

---

We claim:

1. A method of treating damage to pulmonary tissue, said method comprising:
   selecting a subject having pulmonary tissue damage resulting from pulmonary arterial hypertension and
   administering to the subject a therapeutic amount of an Anc80 viral vector comprising a polynucleotide encoding a ceramidase.

2. The method of claim 1, wherein said ceramidase is an acid ceramidase.

3. The method of claim 1, wherein said ceramidase is a neutral ceramidase.

4. The method of claim 1, wherein said ceramidase is an alkaline ceramidase.

5. The method of claim 1, wherein said ceramidase is an ASAH1, an ASAH2, an ASAH2B, an ASAH2C, an ACER1, an ACER2, or an ACER3.

6. The method of claim 1, wherein the polynucleotide encodes an ASAH1 and the ASAH1 comprises an amino acid sequence encoded for by the nucleotide sequence of SEQ ID NO: 1.

7. The method of claim 1, wherein the polynucleotide encodes an ASAH1 and the ASAH1 comprises an amino acid sequence encoded for by the nucleotide sequence of SEQ ID NO: 6.

8. The method of claim 1, wherein the polynucleotide comprises encodes an ASAH1 and the ASAH1 comprises an amino acid sequence encoded for by the nucleotide sequence of SEQ ID NO: 7.

9. The method of claim 1, wherein the Anc80 is aerosolized.

10. The method of claim 1, wherein the administering is intra-tracheal.

* * * * *